(12) United States Patent
Schulz et al.

(10) Patent No.: US 8,901,040 B2
(45) Date of Patent: Dec. 2, 2014

(54) ACTIVE SUBSTANCES FOR INCREASING THE STRESS DEFENSE IN PLANTS TO ABIOTIC STRESS, AND METHODS OF FINDING THEM

(75) Inventors: Arno Schulz, Eppstein-Bremthal (DE); Klaus Bartsch, Königstein (DE); Hansjörg Krähmer, Hofheim (DE); Martin Hills, Idstein (DE); Erwin Hacker, Hochheim (DE); Chris Rosinger, Hofheim am Taunus (DE)

(73) Assignee: Bayer Intellectual Property GmbH, Monheim (DE)

( * ) Notice: Subject to any disclaimer, the term of this patent is extended or adjusted under 35 U.S.C. 154(b) by 630 days.

(21) Appl. No.: 12/826,788

(22) Filed: Jun. 30, 2010

(65) Prior Publication Data

US 2010/0267566 A1    Oct. 21, 2010

Related U.S. Application Data

(63) Continuation of application No. 11/604,214, filed on Nov. 27, 2006, now abandoned.

(30) Foreign Application Priority Data

Nov. 29, 2005  (DE) .......................... 10 2005 057 250

(51) Int. Cl.
| | | |
|---|---|---|
| *A01N 41/06* | (2006.01) | |
| *C12Q 1/68* | (2006.01) | |
| *A01N 37/28* | (2006.01) | |
| *A01N 43/56* | (2006.01) | |
| *A01N 61/00* | (2006.01) | |

(52) U.S. Cl.
CPC ............. *C12Q 1/6895* (2013.01); *A01N 37/28* (2013.01); *A01N 43/56* (2013.01); *A01N 41/06* (2013.01); *A01N 61/00* (2013.01); *C12Q 2600/158* (2013.01)
USPC ......................................... 504/333; 435/6.13

(58) Field of Classification Search
None
See application file for complete search history.

(56) References Cited

U.S. PATENT DOCUMENTS

| | | | |
|---|---|---|---|
| 5,201,931 | A | 4/1993 | Abrams et al. |
| 2001/0001095 | A1 | 5/2001 | Joshi et al. |
| 2004/0018940 | A1* | 1/2004 | Hacker et al. ................. 504/106 |
| 2007/0124839 | A1 | 5/2007 | Schulz et al. |

FOREIGN PATENT DOCUMENTS

| | | |
|---|---|---|
| DE | 3534948 A1 | 4/1987 |
| DE | 277 832 A1 | 4/1990 |
| DE | 277 835 A1 | 4/1990 |
| DE | 41 03 253 A1 | 8/1992 |
| WO | WO 00/28055 A2 | 5/2000 |
| WO | WO 2004/092398 A2 | 10/2004 |

OTHER PUBLICATIONS

Chekker. Printed on Jul. 2, 2014, Bayer CropScience Limited. 6 pages.*
Horus. Printed on Jul. 2, 2014, Bayer CropScience Limited. 12 pages.*
Polecat. Printed on Jul. 2, 2014, Interfarm (UK) Limited. 11 pages.*
Bartlett, D.W., et al., "Review: The strobilurin fungicides," *Pest Manag. Sci.* 60:309, Society of Chemical Industry (Mar. 2004).
Bray, E.A., "Molecular Responses to Water Deficit," *Plant Physiol.* 103:1035-1040, American Society of Plant Physiologists (1993).
Chen, W.P., et al., "Glycinebetaine increases chilling tolerance and reduces chilling-induced lipid peroxidation in Zea mays L.," *Plant Cell Environ.* 23:609-618, Blackwell Science Ltd. (2000).
Cheong, Y.H., et al., "Transcriptional Profiling Reveals Novel Interactions between Wounding, Pathogen, Abiotic Stress, and Hormonal Responses in *Arabidopsis*," *Plant Physiol.* 129:661-677, American Society of Plant Biologists (2002).
Churchill, G.C., et al., "Effects of abscisic acid and abscisic acid analogs on the induction of freezing tolerance of winter rye (*Secale cereale* L.) seedlings," *Plant Growth Reg.* 25:35-45, Kluwer Academic Publishers (1998).
Close, T.J., "Dehydrins: A commonalty in the response of plants to dehydration and low temperature," *Physiol. Plant.* 100:291-296, Physiologia Plantarum (1997).
Hammond-Kosack, K. and Jones, J.D.G., "Responses to Plant Pathogens," in *Biochemistry & Molecular Biology of Plants*, Buchanan, B., et al., eds., American Society of Plant Physiologists, New York, NY, pp. 1102-1156 (2000).
Hasegawa, P.M., et al., "Plant Cellular and Molecular Responses to High Salinity," *Annu. Rev. Plant Physiol. Plant Mol. Biol.* 51:463-499, Annual Reviews (2000).
Ingram, J. and Bartels, D., "The Molecular Basis of Dehydration Tolerance in Plants" *Annu. Rev. Plant Physiol. Plant Mol. Biol.* 47:377-403, Annual Reviews Inc. (1996).

(Continued)

*Primary Examiner* — Anne Gussow
*Assistant Examiner* — Channing S Mahatan
(74) *Attorney, Agent, or Firm* — Sterne Kessler Goldstein & Fox P.L.L.C.

(57) ABSTRACT

The invention relates to a method of finding compounds which increase the tolerance of plants to abiotic stress factors acting on this plant, such as, for example, temperature (such as chill, frost or heat), water (such as dryness, drought or anoxia), or the chemical load (such as lack of or excess of mineral salts, heavy metals, gaseous noxious substances) by increasing the expression of plant-endogenous proteins, and to the use of these compounds for increasing the tolerance in plants to abiotic stress factors.

2 Claims, No Drawings

(56) References Cited

OTHER PUBLICATIONS

Jaglo-Ottosen, K.R., et al., "*Arabidopsis CBF1* Overexpression Induces COR Genes and Enhances Freezing Tolerance," *Science* 280:104-106, American Association for the Advancement of Science (1998).

Kirch, H.-H., et al., "Detailed expression analysis of selected genes of the aldehyde dehydrogenase (ALDH) gene superfamily in *Arabidopsis thaliana*," *Plant Mol. Biol.* 57:315-332, Springer-Verlag (Feb. 2005).

Morrison, M.J. and Andrews, C.J., "Variable Increases in Cold Hardiness Induced in Winter Rape by Plant Growth Regulators," *J. Plant Growth Regul.* 11:113-117, Springer-Verlag New York Inc. (1992).

Rensink, W., et al., "Analyzing the potato abiotic stress transcriptome using expressed sequence tags," *Genome* 48:598-605, NRC Research Press (Aug. 2005).

Yu, J.H., et al., "Biochemical Analysis of a Cytosolic Small Heat Shock Protein, NtHSP18.3, from *Nicotiana tabacum*," *Mol. Cells* 19:328-333, Korean Society for Molecular Biology (Jun. 2005).

Dialog File 351, Accession No. 4005663, English language abstract for DE 3534948 A1, Apr. 9, 1987.

Dialog File 351, Accession No. 5294305, English language abstract for DD 277 832 A1, Apr. 18, 1990.

Dialog File 351, Accession No. 5294308, English language abstract for DD 277 835 A1, Apr. 18, 1990.

Dialog File 351, Accession No. 6033677, English language abstract for DE 4103253 A1, Aug. 6, 1992.

International Search Report for International Application No. PCT/EP2006/010796, European Patent Office, Netherlands, mailed on Jun. 5, 2007.

Hazen, S.P., et al., "Expression profiling of rice segregating for drought tolerance QTLs using a rice genome array," *Funct. Integr. Genomics* 5:104-116, Springer-Verlag (Oct. 2004).

Matsumoto, T.K., "Genes uniquely expressed in vegetative and potassium chlorate induced floral buds of *Dimocarpus longan*," *Plant Sci.* 170:500-510, Elsevier Ireland Ltd. (Mar. 2006).

Denby, K., et al., "Engineering drought and salinity tolerance in plants: lessons from genome-wide expression profiling in *Arabidopsis*," *Trends Biotechnol.* 23547-552, Elsevier Ltd., England (2005).

Kurepa, J., et al., "Differential Expression of CuZn- and Fe-Superoxide Dismutase Genes of Tobacco during Development, Oxidative Stress, and Hormonal Treatments," *Plant Cell Physiol.* 38:463-470, Japanese Society of Plant Physiologists, Japan (1997).

Rensink, W.A., et al., "Microarray expression profiling resources for plant genomics," *Trends Plant Sci.* 10:603-609, Elsevier Ltd., England (2005).

Sánchez, R., et al., "Protein structure modeling for structural genomics," *Nat. Struct. Biol. Suppl.* 7:986-990, Nature America Inc., United States (2000).

Seki, M., et al., "Monitoring the expression profiles of 7000 *Arabidopsis* genes under drought, cold and high-salinity stresses using a full-length cDNA microarray," *Plant J.* 31:279-292, Blackwell Science Ltd., England (2002).

Vranová, E., et al., "Comprehensive analysis of gene expression in *Nicotiana tabacum* leaves acclimated to oxidative stress," *Proc. Natl. Acad. Sci. USA* 99:10870-10875, National Academy of Sciences, United States (2002).

Affymetrix Database search details for MAIZE:ZM.11840.1.A1_AT, downloaded Jul. 29, 2008.

ExPASYy Database search rseults, downloaded Jul. 30, 2008.

NCBI Database, UniGene Zm.11840 *Zea mays* (Maize), downloaded Jul. 29, 2008.

\* cited by examiner

ACTIVE SUBSTANCES FOR INCREASING THE STRESS DEFENSE IN PLANTS TO ABIOTIC STRESS, AND METHODS OF FINDING THEM

The invention relates to a method of finding compounds which increase the tolerance of plants to abiotic stress factors acting on this plant, such as, for example, temperature (such as chill, frost or heat), water (such as dryness, drought or anoxia), or the chemical load (such as lack of or excess of mineral salts, heavy metals, gaseous noxious substances) by increasing the expression of plant-endogenous proteins, and to the use of these compounds for increasing the stress defense in plants to abiotic stress factors.

It is known that plants react with specific or unspecific defense mechanisms to natural stress conditions, such as, for example, chill, heat, drought, wounding, pathogen attack (viruses, bacteria, fungi, insects) and the like, but also to herbicides [Pflanzenbiochemie, pp. 393-462, Spektrum Akademischer Verlag, Heidelberg, Berlin, Oxford, Hans W. Heldt, 1996; Biochemistry and Molecular Biology of Plants, pp. 1102-1203, American Society of Plant Physiologists, Rockville, Md., eds. Buchanan, Gruissem, Jones, 2000].

In plants, there are known a large number of proteins and the genes encoding them which are involved in defense reactions against abiotic stress (for example chill, heat, drought, salt). Some of them belong to signal transduction chains (for example transcription factors, kinases, phosphatases) or they bring about a physiological response of the plant cell (for example ion transport, detoxification of reactive oxygen species). The signal chain genes of the abiotic stress reaction include, inter alia, transcription factors of classes DREB and CBF (Jaglo-Ottosen et al., 1998, Science 280: 104-106). Phosphatases of the ATPK and MP2C type are involved in the salt stress reaction. Furthermore, salt stress frequently activates the biosynthesis of osmolytes such as proline or sucrose. Sucrose synthase and proline transporters (Hasegawa et al., 2000, Annu Rev Plant Physiol Plant Mol Biol 51: 463-499) are examples of those which are involved here. The stress defense of plants to chill and drought utilizes in some cases the same molecular mechanisms. The accumulation of what are known as late emnbryogenesis abundant proteins (LEA proteins), which include the dehydrins as important class (Ingram and Bartels, 1996, Annu Rev Plant Physiol Plant Mol Biol 47: 277-403, Close, 1997, Physiol Plant 100: 291-296), is known. These are chaperones which stabilize the vesicles, proteins and membrane structures in stressed plants (Bray, 1993, Plant Physiol 103: 1035-1040). Moreover, aldehyde dehydrogenases, which detoxify the reactive oxygen species (ROSs) which are generated as the result of oxidative stress, are, moreover, frequently induced (Kirch et al., 2005, Plant Mol Biol 57: 315-332).

Heat shock factors (HSFs) and heat shock proteins (HSPs) are activated under heat stress conditions and as chaperones play a similar role to the dehydrins in the case of chill and drought stress (Yu et al., 2005, Mol Cells 19: 328-333).

Most of the molecular mechanisms described are activated by gene expression being induced. This results in the interesting possibility of characterizing specific stress responses of plants with the aid of transcriptome analysis, for example by gene expression profiling (GEP), with DNA microarrays or with comparable techniques (Rensink et al., 2005, Genome 48: 598-605, Cheong et al., 2002, Plant Physiology 129: 661-677). In this manner, specific stress-reactive gene expression patterns can be recorded and compared with one another.

It is furthermore known that chemical substances can increase the tolerance of plants to abiotic stress. Such substances are applied either by seed dressing, by foliar application or by soil treatment. Thus, increasing the abiotic stress tolerance of crop plants by treatment with elicitors of the systemic acquired resistance (SAR) or with abscisic acid derivatives has been described (Schading and Wei, WO-200028055, Abrams and Gusta, U.S. Pat. No. 5,201,931, Churchill et al., 1998, Plant Growth Regul 25: 35-45).

When applying fungicides, in particular from the strobilurin group, similar effects are also observed, and these frequently also entail increased yields (Draber et al., DE-3534948, Bartlett et al., 2002, Pest Manag Sci 60: 309).

Moreover, there have been described effects of growth regulators on the stress tolerance of crop plants (Morrison and Andrews, 1992, J Plant Growth Regul 11: 113-117, RD-259027). In the case of osmotic stress, a protective effect as the result of the application of osmolytes such as, for example, glycin betaine or their biochemical precursors, for example choline derivatives, has been observed (Chen et al., 2000, Plant Cell Environ 23: 609-618, Bergmann et al., DE-4103253). The effect of antioxidants such as, for example, naphthols and xanthins for increasing the abiotic stress tolerance in plants has also already been described (Bergmann et al., DD-277832, Bergmann et al., DD-277835). However, the molecular causes of the anti-stress effect of the substances are largely unknown.

Thus, it is known that plants have available a plurality of endogenous reaction mechanisms which can bring about an effective defense to a wide range of harmful organisms and/or natural abiotic stress. However, a prediction as to which defense reactions could be provoked or modulated in a targeted fashion by applying active substances was hitherto unknown.

There is therefore a need for a method for the targeted finding of molecular activators of plant-endogenous defense mechanisms to abiotic stress (such as, for example, heat, chill, drought, salinity and acid and base load), whereby novel active substances can be found, novel properties of known, but differently acting, active substances can be identified, or else known molecules or lead structures can be optimized for the use as inductors of the plant-endogenous defense mechanisms to abiotic stress factors.

DEFINITIONS OF TERMS USED HEREINBELOW

The term "BLAST analyses" (Blast=Basic Local Alignment Search Tool)" as used herein describes the use of suitable computer programs for the classification and finding of potentially homologous sequences (Altschul et al., J. Mol. Biol. 1990, 215: 403-410), where an alignment is made between a query sequence and all sequences in one or more databases with specification of a desired agreement in the form of a scoring function (R. Rauhut, Bioinformatik, pp. 38-107, Verlag Wiley-VCH Verlag GmbH, Weinheim, 2001).

The term "cDNA" (complementary DNA) as used in the present context describes a single DNA strand which is complementary to an RNA and which is synthetized in vitro by an enzymatic reverse transcription. The cDNA can correspond either to the total length of the RNA or else only constitute a partial-sequence of the RNA which acts as template.

The term "cluster analysis" as used in the present context means the summary of the individual data obtained by means of a computer program developed for this purpose, where groups of genes which code for proteins with a similar function, or else genes with a similar expression pattern, are shown in a conclusive fashion. This results in a hierarchic minimization of the complex data pattern which can be shown in the form of a dendrogram. The cluster analysis makes possible the classifying assessment of the data sets obtained, which markedly exceeds a mere accumulation of unrelated data.

The terms "DNA chip" and "DNA microarray", which are used synonymously in this context, refer to a support whose matrix consists for example of glass or nylon and whose matrix has DNA fragments fixed to it, where the attachment of the DNA can be effected for example by (a) a photolithographic method (DNA is synthesized directly on the support of the array), (b) a microspotting method (extraneously synthesized oligonucleotides or PCR products are applied to the support and bounded covalently), or (c) by a microspraying method (extraneously synthesized oligonucleotides or PCR products are sprayed onto the support without touching, using an ink-jet printer) (R. Rauhut, Bioinformatik, pp. 197-199, Verlag Wiley-VCH Verlag GmbH, Weinheim, 2001). A DNA chip which represents genomic sequences of an organism is referred to as a "genomic DNA chip". The evaluation of the data obtained with these "DNA chips" is referred to as "DNA chip analysis".

The term "DNA chip hybridization" as used in the present context means the pairing of two single-stranded, complementary nucleic acid molecules, where one of the base-pairing molecule partners is located on the DNA chip as DNA (deoxyribonucleic acid) in preferably covalently bonded form, while the other is in solution in the form of the RNA (ribonucleic acid) or the corresponding cDNA (complementary DNA). The hybridization of the bonded and unbonded nucleic acids on the DNA chip takes place in aqueous buffer solution, if appropriate under additionally denaturing conditions such as, for example, in the presence of dimethyl sulfoxide, at temperatures of 30-60° C., preferably 40-50° C., especially preferably at 45° C. for 10-20 hours, preferably for 14-18 hours, especially preferably for 16 hours, with constant movement. The hybridization conditions can be established in a constant fashion for example in a hybridization oven. Standard movements of 60 rpm (rounds per minute, revolutions per minute) are produced in such a hybridization oven.

The nucleic acid sequence referred to by the term "EST sequence" (expressed sequence tag) means, in the present context, a short sequence of 200-500 bases or base pairs.

The terms "expression pattern", "induction pattern" and "expression profile", which are used synonymously describe, in the present context, the expression differentiated over time and/or the tissue-specific expression of the plant mRNA, the pattern being obtained directly by the generated intensity of the hybridization signal of the RNA obtained from the plant or its corresponding cDNA with the aid of the DNA chip technology. The measured "induction values" are obtained by direct numerical processing with the corresponding signals which are obtained by using a synonymous chip, with the hybridization with an untreated/stressed control plant.

The term "expression state" which is obtained by the "gene expression profiling" which has been carried out describes, in the present context, all of the recorded transcriptional activity of cellular genes which is measured with the aid of a DNA chip.

The term "total RNA" as used in the present context describes the representation, which is possible as the result of the disruption method applied, of different plant-endogenous RNA groups which can be present in a plant cell, such as, for example, cytoplasmic rRNA (ribosomal RNA), cytoplasmic tRNA (transfer RNA), cytoplasmic mRNA (messenger RNA) and their respective nuclear precursors, ctRNA (chloroplastidial RNA) and mtRNA (mitochondrial RNA), but it also comprises RNA molecules which can be obtained from exogenous organisms, such as, for example, viruses, or from parasitic bacteria and fungi.

The term "useful plants" means, in the present context, crop plants which are employed as plants for obtaining foodstuffs, feedstuffs or for industrial purpose.

The term "safener" as used in the present context refers to a chemical compound which is of non-plant-endogenous origin and which compensates for, or reduces, the phytotoxic properties of a pesticide in relation to useful plants, without substantially reducing the pesticidal activity in relation to harmful organisms such as, for example, weeds, bacteria, viruses and fungi.

Safeners which, in addition to their function for which they are known per se, also contribute to increasing the tolerance to abiotic stress factors are preferably selected from the group defined hereinbelow, it being possible to select different safeners depending on the abiotic stress factor, and it being possible to use only a single safener or else a plurality of safeners from the same group or from different groups:

a) compounds of the formulae (I) to (III),

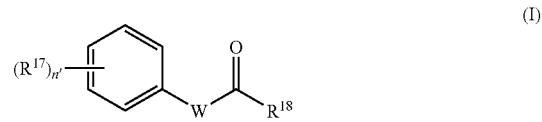

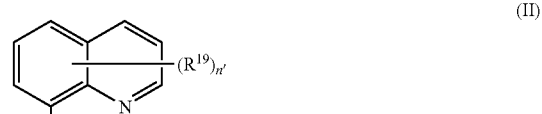

where the symbols and indices have the following meanings:

n' is a natural number from 0 to 5, preferably 0 to 3;

T is a ($C_1$ or $C_2$)alkanediyl chain which is unsubstituted or substituted by one or two ($C_1$-$C_4$)alkyl radicals or with [($C_1$-$C_3$)alkoxy]carbonyl;

W is an unsubstituted or substituted divalent heterocyclic radical selected from the group of the partially unsaturated or aromatic five-membered heterocycles with 1 to 3 hetero ring atoms of the N or O type, where the ring contains at least one nitrogen atom and not more than one oxygen atom, preferably a radical selected from the group (W1) to (W4),

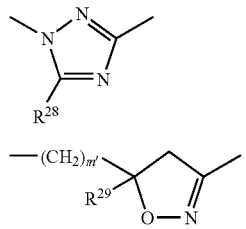
(W3)

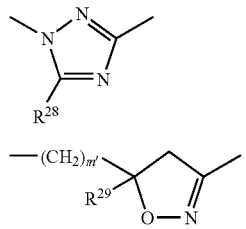
(W4)

m' is 0 or 1;

$R^{17}$, $R^{19}$ are identical or different and are halogen, $(C_1-C_4)$alkyl, $(C_1-C_4)$alkoxy, nitro or $(C_1-C_4)$haloalkyl;

$R^{18}$, $R^{20}$ are identical or different and are $OR^{24}$, $SR^{24}$ or $NR^{24}R^{25}$ or a saturated or unsaturated 3- to 7-membered heterocycle having at least one nitrogen atom and up to 3 heteroatoms, preferably selected from the group consisting of O and S, which heterocycle is linked with the carbonyl group (II) or (III) via the nitrogen atom and is unsubstituted or substituted by radicals selected from the group consisting of $(C_1-C_4)$alkyl, $(C_1-C_4)$alkoxy or optionally substituted phenyl, preferably a radical of the formula $OR^{24}$, $NHR^{25}$ or $N(CH_3)_2$, in particular of the formula $OR^{24}$;

$R^{24}$ is hydrogen or an unsubstituted or substituted aliphatic hydrocarbon radical, preferably having a total of 1 to 18 carbon atoms;

$R^{25}$ is halogen, $(C_1-C_6)$alkyl, $(C_1-C_6)$alkoxy or substituted or unsubstituted phenyl;

$R^X$ is H, $(C_1-C_8)$alkyl, $(C_1-C_8)$haloalkyl, $(C_1-C_4)$alkoxy$(C_1-C_8)$alkyl, cyano or $COOR^{26}$, where $R^{26}$ is hydrogen, $(C_1-C_8)$alkyl, $(C_1-C_8)$haloalkyl, $(C_1-C_4)$alkoxy-$(C_1-C_4)$alkyl, $(C_1-C_6)$hydroxyalkyl, $(C_3-C_{12})$cycloalkyl or tri$(C_1-C_4)$alkylsilyl;

$R^{27}$, $R^{28}$, $R^{29}$ are identical or different and are hydrogen, $(C_1-C_8)$alkyl, $(C_1-C_8)$haloalkyl, $(C_3-C_{12})$cycloalkyl or substituted or unsubstituted phenyl;

$R^{21}$ is $(C_1-C_4)$alkyl, $(C_1-C_4)$haloalkyl, $(C_2-C_4)$alkenyl, $(C_2-C_4)$haloalkenyl, $(C_3-C_7)$cycloalkyl, preferably dichloromethyl;

$R^{22}$, $R^{23}$ are identical or different and are hydrogen, $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_1-C_4)$alkylcarbamoyl-$(C_1-C_4)$alkyl, $(C_2-C_4)$alkenylcarbamoyl$(C_1-C_4)$alkyl, $(C_1-C_4)$alkoxy-$(C_1-C_4)$alkyl, dioxolanyl$(C_1-C_4)$alkyl, thiazolyl, furyl, furylalkyl, thienyl, piperidyl, substituted or unsubstituted phenyl, or $R^{22}$ and $R^{23}$ together form a substituted or unsubstituted heterocyclic ring, preferably an oxazolidine, thiazolidine, piperidine, morpholine, hexahydropyrimidine or benzoxazine ring;

b) one or more compounds from the group consisting of:
1,8-naphthalic anhydride, methyldiphenyl methoxyacetate,
1-(2-chlorobenzyl)-3-(1-methyl-1-phenylethyl)urea (cumyluron),
O,O-diethyl S-2-ethylthioethyl phosphorodithioate (disulfoton),
4-chlorophenyl methylcarbamate (mephenate),
O,O-diethyl O-phenyl phosphorothioate (dietholate),
4-carboxy-3,4-dihydro-2H-1-benzopyran-4-acetic acid (CL-304415, CAS-Reg. No: 31541-57-8),
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolane (MG-191),
N-(4-methylphenyl)-N'-(1-methyl-1-phenylethyl)urea (dymron),
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor)
and their salts and esters, preferably $(C_1-C_8)$;

c) N-acylsulfonamides of the formula (IV) and their salts,

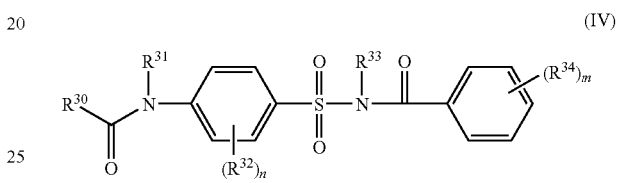

in which $R^{30}$ is hydrogen, a hydrocarbon radical, an oxyhydrocarbon radical, a thiohydrocarbon radical or a heterocyclyl radical which is preferably bonded via a carbon atom, for each of the last-mentioned 4 radicals is unsubstituted or substituted by one or more identical or different radicals selected from the group consisting of halogen, cyano, nitro, amino, hydroxyl, carboxyl, formyl, carboxamide, sulfonamide and radicals of the formula $-Z^a-R^a$, where each hydrocarbon moiety preferably has 1 to 20 carbon atoms and a carbon-containing radical $R^{30}$ including substituents preferably has 1 to 30 carbon atoms;

$R^{31}$ is hydrogen or $(C_1-C_4)$alkyl, preferably hydrogen, or $R^{30}$ and $R^{31}$ together with the group of the formula $-CO-N-$ are the radical of the 3- to 8-membered saturated or unsaturated ring;

$R^{32}$ radicals are identical or different and are halogen, cyano, nitro, amino, hydroxyl, carboxyl, formyl, $CONH_2$, $SO_2NH_2$ or a radical of the formula $-Z^b-R^b$;

$R^{33}$ is hydrogen or $(C_1-C_4)$alkyl, preferably H;

$R^{34}$ radicals are identical or different and are halogen, cyano, nitro, amino, hydroxyl, carboxyl, CHO, $CONH_2$, $SO_2NH_2$ or a radical of the formula $-Z^c-R^c$;

$R^a$ is a hydrocarbon radical or heterocyclyl radical, where each of the two last-mentioned radicals is unsubstituted or substituted by one or more identical or different radicals selected from the group consisting of halogen, cyano, nitro, amino, hydroxyl, mono- and di[$(C_1-C_4)$alkyl]amino, or an alkyl radical in which a plurality of, preferably 2 or 3, non-adjacent $CH_2$ groups are in each case replaced by one oxygen atom;

$R^b, R^c$ are identical or different hydrocarbon radicals or heterocyclyl radicals, where each of the two last-mentioned radicals is unsubstituted or substituted by one or more identical or different radicals selected from the group consisting of halogen, cyano, nitro, amino, hydroxyl, phosphoryl, halo$(C_1-C_4)$alkoxy, mono- and di[$(C_1-C_4)$alkyl]amino, or an alkyl radical in which a plurality of, preferably 2 or 3, non-adjacent $CH_2$ groups are in each case replaced by one oxygen atom;

$Z^a$ is a divalent group of the formula —O—, —S—, —CO—, —CS—, —CO—O—, —CO—S—, —O—CO—, —S—CO—, —SO—, —SO$_2$—, —NR*—, —CO—NR*—, —NR*—CO—, —SO$_2$—NR*— or —NR*—SO$_2$—, where the bond indicated on the right-hand side of the respective divalent group is the bond with the radical $R^a$ and where the R* radicals in the last-mentioned 5 radicals independently of one another are in each case H, $(C_1-C_4)$alkyl or halo$(C_1-C_4)$alkyl;

$Z^b, Z^c$ independently of one another are a direct bond or a divalent group of the formula —O—, —S—, —CO—, —CS—, —CO—O—, —CO—S—, —O—CO—, —S—CO—, —SO—, —SO$_2$—, —NR*—, —SO$_2$—NR*—, —NR*—SO$_2$—, —CO—NR*- or —NR*—CO—, where the bond indicated on the right-hand side of the respective divalent group is the bond with the radical $R^b$ or $R^c$ and where the R* radicals in the last-mentioned 5 radicals independently of one another are in each case H, $(C_1-C_4)$alkyl or halo$(C_1-C_4)$alkyl;

n is an integer from 0 to 4, preferably 0, 1 or 2, in particular 0 or 1, and m is an integer from 0 to 5, preferably 0, 1, 2 or 3, in particular 0, 1 or 2;

d) acylsulfamoylbenzamides of the general formula (V), if appropriate also in salt form,

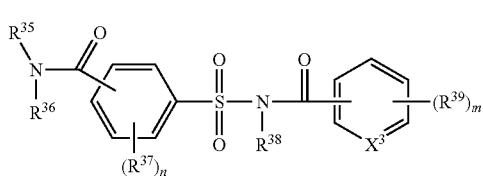

(V)

where $X^3$ is CH or N;

$R^{35}$ is hydrogen, heterocyclyl or a hydrocarbon radical, where the two last-mentioned radicals are optionally substituted by one or more, identical or different radicals selected from the group consisting of halogen, cyano, nitro, amino, hydroxyl, carboxyl, CHO, CONH$_2$, SO$_2$NH$_2$ and $Z^a$—$R^a$;

$R^{36}$ is hydrogen, hydroxyl, $(C_1-C_6)$alkyl, $(C_2-C_6)$alkenyl, $(C_2-C_6)$alkynyl, $(C_1-C_6)$alkoxy, $(C_2-C_6)$alkenyloxy, where the five last-mentioned radicals are optionally substituted by one or more, identical or different radicals selected from the group consisting of halogen, hydroxyl, $(C_1-C_4)$alkyl, $(C_1-C_4)$alkoxy and $(C_1-C_4)$alkylthio, or $R^{35}$ and $R^{36}$ together with the nitrogen atom to which they are attached are a 3- to 8-membered saturated or unsaturated ring;

$R^{37}$ is halogen, cyano, nitro, amino, hydroxyl, carboxyl, CHO, CONH$_2$, SO$_2$NH$_2$ or $Z^b$—$R^b$;

$R^{38}$ is hydrogen, $(C_1-C_4)$alkyl, $(C_2-C_4)$alkenyl or $(C_2-C_4)$alkynyl;

$R^{39}$ is halogen, cyano, nitro, amino, hydroxyl, carboxyl, phosphoryl, CHO, CONH$_2$, SO$_2$NH$_2$ or $Z^c$—$R^c$;

$R^a$ is a $(C_2-C_{20})$alkyl radical whose carbon chain is interrupted once or more than once by oxygen atoms, or is heterocyclyl or a hydrocarbon radical, where the two last-mentioned radicals are optionally substituted by one or more, identical or different radicals selected from the group consisting of halogen, cyano, nitro, amino, hydroxyl, mono- and di[$(C_1-C_4)$alkyl]amino;

$R^b$, $R^c$ are a $(C_2-C_{20})$alkyl radical whose carbon chain is interrupted once or more than once by oxygen atoms, or is heterocyclyl or a hydrocarbon radical, where the two last-mentioned radicals are optionally substituted by one or more, identical or different radicals selected from the group consisting of halogen, cyano, nitro, amino, hydroxyl, phosphoryl, $(C_1-C_4)$haloalkoxy, mono- and di[$(C_1-C_4)$alkyl]amino;

$Z^a$ is a divalent unit selected from the group consisting of O, S, CO, CS, C(O)O, C(O)S, SO, SO$_2$, NR$^d$, C(O)NR$^d$ or SO$_2$NR$^d$;

$Z^b$, $Z^c$ are identical or different and are a direct bond or a divalent unit selected from the group consisting of O, S, CO, CS, C(O)O, C(O)S, SO, SO$_2$, NR$^d$, SO$_2$NR$^d$ or C(O)NR$^d$;

$R^d$ is hydrogen, $(C_1-C_4)$alkyl or $(C_1-C_4)$haloalkyl;

n is an integer from 0 to 4, and m, in the event that X is CH, is an integer from 0 to 5 and in the event that X is N, an integer from 0 to 4;

e) compounds of the acylsulfamoylbenzamide type, for example of the formula (VI) hereinbelow, some of which are known from WO 99/16744,

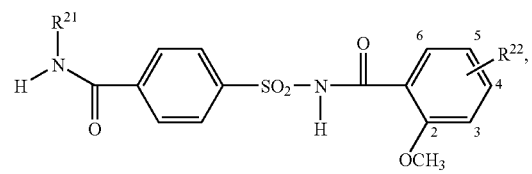

(VI)

for example those in which $R^{21}$=cyclopropyl and $R^{22}$=H (S3-1=4-cyclopropylaminocarbonyl-N-(2 methoxybenzoyl)benzenesulfonamide), $R^{21}$=cyclopropyl and $R^{22}$=5-Cl (S3-2), $R^{21}$=ethyl and $R^{22}$=H (S3-3), $R^{21}$=isopropyl and $R^{22}$=5-Cl (S3-4) and $R^{21}$=isopropyl and $R^{22}$=H (S3-5);

f) Compounds of the N-acylsulfamoylphenylurea type of the formula (VII), some of which are known from EP-A-365484,

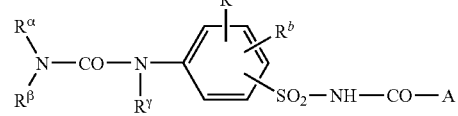

(VII)

where

A is a radical selected from the group consisting of

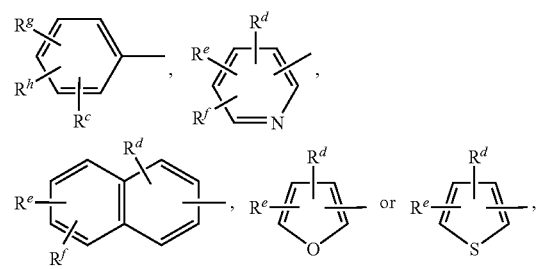

$R^\alpha$ and $R^\beta$ independently of one another are hydrogen, $C_1$-$C_8$-alkyl, $C_3$-$C_8$-cycloalkyl, $C_3$-$C_6$-alkenyl, $C_3$-$C_6$-alkynyl,

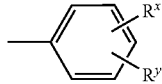

or $C_1$-$C_4$-alkoxy which is substituted by $C_1$-$C_4$-alkoxy or by

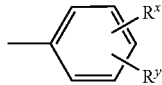

$R^\alpha$ and $R^\beta$ together are a $C_4$-$C_6$-alkylene bridge or a $C_4$-$C_6$-alkylene bridge which is interrupted by oxygen, sulfur, SO, $SO_2$, NH or —N($C_1$-$C_4$-alkyl)-, $R^\gamma$ is hydrogen or $C_1$-$C_4$-alkyl, $R^a$ and $R^b$ independently of one another are hydrogen, halogen, cyano, nitro, trifluoromethyl, $C_1$-$C_4$-alkyl, $C_1$-$C_4$-alkoxy, $C_1$-$C_4$-alkylthio, $C_1$-$C_4$-alkylsulfinyl, $C_1$-$C_4$-alkylsulfonyl, —$COOR^j$, —$CONR^kR^m$, —$COR^n$, —$SO_2NR^kR^m$, or —$OSO_2$—$C_1$-$C_4$-alkyl, or $R^a$ and $R^b$ together are a $C_3$-$C_4$-alkylene bridge which can be substituted by halogen or $C_1$-$C_4$-alkyl, or a $C_3$-$C_4$-alkenylene bridge which can be substituted by halogen or $C_1$-$C_4$-alkyl, or a $C_4$-alkadienylene bridge which can be substituted by halogen or $C_1$-$C_4$-alkyl, and $R^g$ and $R^h$ independently of one another are hydrogen, halogen, $C_1$-$C_4$-alkyl, trifluoromethyl, methoxy, methylthio or —$COOR^j$, where $R^c$ is hydrogen, halogen, $C_1$-$C_4$-alkyl or methoxy, $R^d$ is hydrogen, halogen, nitro, $C_1$-$C_4$-alkyl, $C_1$-$C_4$-alkoxy, $C_1$-$C_4$-alkylthio, $C_1$-$C_4$-alkylsulfinyl, $C_1$-$C_4$-alkylsulfonyl, —$COOR^j$ or —$CONR^kR^m$, $R^e$ is hydrogen, halogen, $C_1$-$C_4$-alkyl, —$COOR^j$, trifluoromethyl or methoxy, or $R^d$ and $R^e$ together are a $C_3$-$C_4$-alkylene bridge, $R^f$ is hydrogen, halogen or $C_1$-$C_4$-alkyl, $R^X$ and $R^Y$ independently of one another are hydrogen, halogen, $C_1$-$C_4$-alkyl, $C_1$-$C_4$-alkoxy, $C_1$-$C_4$-alkylthio, —$COOR^j$, trifluoromethyl, nitro or cyano, $R^j$, $R^k$ and $R^m$ independently of one another are hydrogen or $C_1$-$C_4$-alkyl, $R^k$ and $R^m$ together are a $C_4$-$C_6$-alkylene bridge or a $C_4$-$C_6$-alkylene bridge which is interrupted by oxygen, NH or —N($C_1$-$C_4$-alkyl)-, and $R^n$ is $C_1$-$C_4$-alkyl, phenyl or phenyl which is substituted by halogen, $C_1$-$C_4$-alkyl, methoxy, nitro or trifluoromethyl, preferably 1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthoylsulfamoyl)phenyl]-3,3-dimethylurea, g) compounds of the acylsulfamoylbenzamide type of the formula (VIII), disclosed in EP-A-1019368, if appropriate also in salt form,

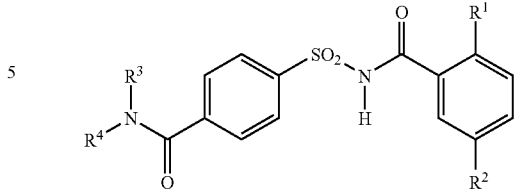

where
$R^1$ is methyl, methoxy or trifluoromethoxy;
$R^2$ is hydrogen, chlorine or methyl;
$R^3$ is hydrogen, ethyl or propargyl;
$R^4$ is ethyl, cyclopropyl, iso-propyl or propargyl,
or
$R^3$ and $R^4$ together form the group $(CH_2)_4$,
including the stereoisomers and including the salts which are conventionally used in agriculture.

The compounds of the formula (I) are disclosed for example in EP-A-0 333 131 (ZA-89/1960), EP-A-0 269 806 (U.S. Pat. No. 4,891,057), EP-A-0 346 620 (AU-A-89/34951), EP-A-0 174 562, EP-A-0 346 620 (WO-A-91/08 202), WO-A-91/07 874 or WO-A 95/07 897 (ZA 94/7120) and the literature cited therein or can be prepared by, or in analogy with, the processes described therein.

The compounds of the formula (II) are disclosed for example in EP-A-0 086 750, EP-A-0 94349 (U.S. Pat. No. 4,902,340), EP-A-0 191736 (U.S. Pat. No. 4,881,966) and EP-A-0 492 366 and the literature cited therein or can be prepared by, or in analogy with, the processes described therein. Some compounds are furthermore described in EP-A-0 582 198 and WO 2002/34048.

The compounds of the formula (III) are known from a large number of patent applications, for example U.S. Pat. No. 4,021,224 and U.S. Pat. No. 4,021,229.

Compounds of group (b) are furthermore known from CN-A-87/102 789, EP-A-365484 and from "The Pesticide Manual", The British Crop Protection Council and the Royal Society of Chemistry, 11th edition, Farnham 1997.

The compounds of group (c) are described in WO-A-97/45016, those of group (d) in WO-A-99/16744, those of group B (e) in EP-A-365484 and those of group (g) in EP-A-1019368.

The publications cited contain extensive information on preparation processes and starting materials and detail preferred compounds. These publications are expressly referred to herewith; they are incorporated into the present description by reference.

Preferred compounds of the formula (I) and/or (II) which are known as safeners are those in which the symbols and indices have the following meanings:

$R^{24}$ is hydrogen, $(C_1$-$C_{18})$alkyl, $(C_3$-$C_{12})$cycloalkyl, $(C_2$-$C_8)$alkenyl and $(C_2$-$C_{18})$alkynyl, where the carbon-containing groups can be substituted by one or more, preferably up to three, radicals $R^{50}$;

$R^{50}$ is identical or different and is halogen, hydroxyl, $(C_1$-$C_8)$alkoxy, $(C_1$-$C_8)$alkylthio, $(C_2$-$C_8)$alkenylthio, $(C_2$-$C_8)$alkynylthio, $(C_2$-$C_8)$alkenyloxy, $(C_2$-$C_8)$alkynyloxy, $(C_3$-$C_7)$cycloalkyl, $(C_3$-$C_7)$cycloalkoxy, cyano, mono- and di(($C_1$-$C_4$)alkyl)amino, carboxyl, $(C_1$-$C_8)$alkoxycarbonyl, $(C_2$-$C_8)$alkenyloxycarbonyl, $(C_1$-$C_8)$alkylthiocarbonyl, $(C_2$-$C_8)$alkynyloxycarbonyl, $(C_1$-$C_8)$alkylcarbonyl, $(C_2$-$C_8)$alkenylcarbonyl, $(C_2$-$C_8)$alkynylcarbonyl, 1-(hydroxyimino)$(C_1$-$C_6)$alkyl, 1-[($C_1$-$C_4$)alkylimino]-$(C_1$-$C_4$)alkyl, 1-[($C_1$-$C_4$)alkoxyimino]$(C_1$-$C_6$)alkyl, $(C_1$-$C_8)$alkylcarbonylamino, $(C_2-C_8)$alkenylcarbonylamino, $(C_2-C_8)$alkynylcarbonylamino, aminocarbonyl, $(C_1-C_8)$alkylaminocarbonyl, di$(C_1-C_6)$alkylaminocarbonyl, $(C_2-C_6)$alkenylaminocarbonyl, $(C_2-C_6)$alkynylaminocarbonyl, $(C_1-C_8)$alkoxycarbonylamino, $(C_1-C_8)$alkylaminocarbonylamino, $(C_1-C_6)$alkylcarbonyloxy which is unsubstituted or substituted by $R^{51}$, or are $(C_2-C_6)$alkenylcarbonyloxy, $(C_2-C_6)$alkynylcarbonyloxy, $(C_1-C_8)$alkylsulfonyl, phenyl, phenyl$(C_1-C_6)$alkoxy, phenyl$(C_1-C_6)$alkoxycarbonyl, phenoxy, phenoxy$(C_1-C_6)$alkoxy, phenoxy$(C_1-C_6)$alkoxycarbonyl, phenylcarbonyloxy, phenylcarbonylamino, phenyl$(C_1-C_6)$alkylcarbonylamino, where the 9 last-mentioned radicals are unsubstituted or mono- or polysubstituted, preferably up to trisubstituted, in the phenol ring by radicals $R^{52}$; SiR'$_3$, —O—SiR'$_3$, R'$_3$Si$(C_1-C_8)$alkoxy, —CO—O—NR'$_2$, —O—N=CR'$_2$, —N=CR'$_2$, —O—NR'$_2$, —NR'$_2$, CH(OR')$_2$, —O—(CH$_2$)$_m$—CH(OR')$_2$, —CR'''(OR')$_2$, —O—(CH$_2$)$_m$CR'''(OR'')$_2$ or by R''O—CHR'''CHCOR''—$(C_1-C_6)$alkoxy, $R^{51}$ is identical or different and is halogen, nitro, $(C_1-C_4)$alkoxy and phenyl which is unsubstituted or substituted by one or more, preferably up to three, radicals $R^{52}$;

$R^{52}$ is identical or different and is halogen, $(C_1-C_4)$alkyl, $(C_1-C_4)$alkoxy, $(C_1-C_4)$haloalkyl, $(C_1-C_4)$haloalkoxy or nitro;

R' is identical or different and is hydrogen, $(C_1-C_4)$alkyl, unsubstituted phenyl or phenyl which is substituted by one or more, preferably by up to three, radicals $R^{52}$, or two radicals R' together form a $(C_2-C_6)$alkanediyl chain;

R'' is identical or different and is $(C_1-C_4)$alkyl, or two radicals R'' together form a $(C_2-C_6)$alkanediyl chain;

R''' is hydrogen or $(C_1-C_4)$alkyl;

m is 0, 1, 2, 3, 4, 5 or 6.

Especially preferred compounds of the formula (I) and (II) which are known as safeners are those in which the symbols and indices have the following meanings:

$R^{24}$ is hydrogen, $(C_1-C_8)$alkyl or $(C_3-C_7)$cycloalkyl, where the above carbon-containing radicals are unsubstituted or mono- or polysubstituted by halogen or mono- or disubstituted, preferably monosubstituted, by radicals $R^{50}$, $R^{50}$ is identical or different and is hydroxyl, $(C_1-C_4)$alkoxy, carboxyl, $(C_1-C_4)$alkoxycarbonyl, $(C_2-C_6)$alkenyloxycarbonyl, $(C_2-C_6)$alkynyloxycarbonyl, 1-(hydroxyimino)$(C_1-C_4)$alkyl, 1-[$(C_1-C_4)$alkylimino]$(C_1-C_4)$alkyl and 1-[$(C_1-C_4)$alkoxyimino]$(C_1-C_4)$alkyl; —SiR'$_3$, —O—N=CR'$_2$, —N=CR'$_2$, —NR'$_2$, and —O—NR'$_2$, where R' is identical or different and is hydrogen, $(C_1-C_4)$alkyl or in groups of two is a $(C_4-C_5)$alkanediyl chain, $R^{27}$, $R^{28}$, $R^{29}$ are identical or different and are hydrogen, $(C_1-C_8)$alkyl, $(C_1-C_6)$haloalkyl, $(C_3-C_7)$cycloalkyl or phenyl which is unsubstituted or substituted by one or more radicals selected from the group consisting of halogen, cyano, nitro, amino, mono- and di[$(C_1-C_4)$alkyl]amino, $(C_1-C_4)$alkyl, $(C_1-C_4)$haloalkyl, $(C_1-C_4)$alkoxy, $(C_1-C_4)$haloalkoxy, $(C_1-C_4)$alkylthio and $(C_1-C_4)$alkylsulfonyl;

$R^x$ is hydrogen or COOR$^{26}$, where $R^{26}$ is hydrogen, $(C_1-C_8)$alkyl, $(C_1-C_8)$haloalkyl, $(C_1-C_4$-alkoxy)$(C_1-C_4)$alkyl, $(C_1-C_6)$hydroxyalkyl, $(C_3-C_7)$cycloalkyl or tri$(C_1-C_4)$alkylsilyl, $R^{17}$, $R^{19}$ are identical or different and are halogen, methyl, ethyl, methoxy, ethoxy, $(C_1$ or $C_2)$haloalkyl, preferably hydrogen, halogen or $(C_1$ or $C_2)$haloalkyl.

Very especially preferred compounds which are known as safeners are those in which the symbols and indices in formula (I) have the following meanings:

$R^{17}$ is halogen, nitro or $(C_1-C_4)$haloalkyl;

n' is 0, 1, 2 or 3;

$R^{18}$ is a radical of the formula OR$^{24}$, $R^{24}$ is hydrogen, $(C_1-C_8)$alkyl or $(C_3-C_7)$cycloalkyl, where the above carbon-containing radicals are unsubstituted or mono- or polysubstituted, preferably up to trisubstituted, by identical or different halogen radicals or up to disubstituted, preferably monosubstituted, by identical or different radicals selected from the group consisting of hydroxyl, $(C_1-C_4)$alkoxy, $(C_1-C_4)$alkoxycarbonyl, $(C_2-C_6)$alkenyloxycarbonyl, $(C_2-C_6)$alkynyloxycarbonyl, 1-(hydroxyimino)$(C_1-C_4)$alkyl, 1-[$(C_1-C_4)$alkylimino]$(C_1-C_4)$alkyl, 1-[$(C_1-C_4)$alkoxyimino]$(C_1-C_4)$alkyl and radicals of the formulae —SiR'$_3$, —O—N=R'$_2$, —N=CR'$_2$, —NR'$_2$ and —O—NR'$_2$, where the radicals R' in the above formulae are identical or different and are hydrogen, $(C_1-C_4)$alkyl or in groups of two are $(C_4$ or $C_5)$alkanediyl;

$R^{27}$, $R^{28}$, $R^{29}$ are identical or different and are hydrogen, $(C_1-C_8)$alkyl, $(C_1-C_8)$haloalkyl, $(C_3-C_7)$cycloalkyl or phenyl which is unsubstituted or substituted by one or more of the radicals selected from the group consisting of halogen, $(C_1-C_4)$alkyl, $(C_1-C_4)$alkoxy, nitro, $(C_1-C_4)$haloalkyl and $(C_1-C_4)$haloalkoxy, and $R^x$ is hydrogen or COOR$^{26}$, where $R^{26}$ is hydrogen, $(C_1-C_8)$alkyl, $(C_1-C_8)$haloalkyl, $(C_1-C_4)$alkoxy$(C_1-C_4)$alkyl, $(C_1-C_6)$hydroxyalkyl, $(C_3-C_7)$cycloalkyl or tri$(C_1-C_4)$alkylsilyl.

Also very especially preferred compounds of the formula (II) which are known as safeners are those in which the symbols and indices have the following meanings:

$R^{19}$ is halogen or $(C_1-C_4)$haloalkyl;

n' is 0, 1, 2 or 3, where $(R^{19})_{n'}$ is preferably 5-Cl;

$R^{20}$ is a radical of the formula OR$^{24}$;

T is CH$_2$ or CH(COO—$(C_1-C_3$-alkyl)) and $R^{24}$ is hydrogen, $(C_1-C_8)$alkyl, $(C_1-C_8)$haloalkyl or $(C_1-C_4)$alkoxy$(C_1-C_4)$alkyl, preferably hydrogen or $(C_1-C_8)$alkyl.

In this context, particularly preferred compounds of the formula (I) which are known as safeners are those in which the symbols and indices have the following meanings:

W is (W1);

$R^{17}$ is halogen or $(C_1-C_2)$haloalkyl;

n' is 0, 1, 2 or 3, where $(R^{17})_{n'}$ is preferably 2,4-Cl$_2$;

$R^{18}$ is a radical of the formula OR$^{24}$;

$R^{24}$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy$(C_1-C_4)$alkyl or tri$(C_1-C_2)$alkylsilyl, preferably $(C_1-C_4)$alkyl;

$R^{27}$ is hydrogen, $(C_1-C_8)$alkyl, $(C_1-C_4)$haloalkyl or $(C_3-C_7)$cycloalkyl, preferably hydrogen or $(C_1-C_4)$alkyl, and $R^x$ is COOR$^{26}$, where $R^{26}$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy$(C_1-C_4)$alkyl or tri$(C_1-C_2)$alkylsilyl, preferably hydrogen or $(C_1-C_4)$alkyl.

Other particularly preferred compounds of the formula (I) which are known as safeners are those in which the symbols and indices have the following meanings:

W is (W2);

$R^{17}$ is halogen or $(C_1-C_2)$haloalkyl;

n' is 0, 1, 2 or 3, where $(R^{17})_{n'}$ is preferably 2,4-Cl$_2$;

$R^{18}$ is a radical of the formula OR$^{24}$;

$R^{24}$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy$(C_1-C_4)$alkyl or tri$(C_1-C_2)$alkylsilyl, preferably $(C_1-C_4)$alkyl, and $R^{27}$ is hydrogen, $(C_1-C_8)$alkyl, $(C_1-C_4)$haloalkyl, $(C_3-C_7)$cycloalkyl or unsubstituted or substituted phenyl, preferably hydrogen, $(C_1-C_4)$alkyl or phenyl which is unsubstituted or substituted by one or more radicals selected from the group consisting of halogen, $(C_1-C_4)$alkyl, $(C_1-C_4)$haloalkyl, nitro, cyano or $(C_1-C_4)$alkoxy.

Other particularly preferred compounds of the formula (I) which are known as safeners are those in which the symbols and indices have the following meanings:

W is (W3);
$R^{17}$ is halogen or $(C_1-C_2)$haloalkyl;
n' is 0, 1, 2 or 3, where $(R^{17})_{n'}$ is preferably 2,4-$Cl_2$;
$R^{18}$ is a radical of the formula $OR^{24}$;
$R^{24}$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy$(C_1-C_4)$alkyl or tri$(C_1-C_2)$alkylsilyl, preferably $(C_1-C_4)$alkyl, and
$R^{28}$ is $(C_1-C_8)$alkyl or $(C_1-C_4)$haloalkyl, preferably $C_1$-haloalkyl.

Other especially preferred compounds of the formula (I) which are known as safeners are those in which the symbols and indices have the following meanings:

W is (W4);
$R^{17}$ is halogen, nitro, $(C_1-C_4)$alkyl, $(C_1-C_2)$haloalkyl, preferably $CF_3$, or $(C_1-C_4)$alkoxy;
n' is 0, 1, 2 or 3;
m' is 0 or 1;
$R^{18}$ is a radical of the formula $OR^{24}$;
$R^{24}$ is hydrogen, $(C_1-C_4)$alkyl, carboxy$(C_1-C_4)$alkyl, $(C_1-C_4)$alkoxycarbonyl$(C_1-C_4)$alkyl, preferably $(C_1-C_4)$alkoxy-CO—$CH_2$—, $(C_1-C_4)$alkoxy-CO—$C(CH_3)H$—, HO—CO—$CH_2$— or HO—CO—$C(CH_3)H$—, and
$R^{29}$ is hydrogen, $(C_1-C_4)$alkyl, $(C_1-C_4)$haloalkyl, $(C_3-C_7)$cycloalkyl or phenyl which is unsubstituted or substituted by one or more radicals selected from the group consisting of halogen, $(C_1-C_4)$alkyl, $(C_1-C_4)$haloalkyl, nitro, cyano and $(C_1-C_4)$alkoxy.

The following groups of compounds which are known as safeners are particularly suitable as active substances for increasing the tolerance of plants to abiotic stress factors:

a) compounds of the dichlorophenylpyrazoline-3-carboxylic acid type (i.e. of the formula (I) in which W=(W1) and $(R^{17})_n=2,4-Cl_2$), preferably compounds such as ethyl 1-(2,4-dichlorophenyl)-5-(ethoxycarbonyl)-5-methyl-2-pyrazoline-3-carboxylate (I-1, mefenpyr-diethyl), mefenpyr-dimethyl and mefenpyr (I-0), and related compounds as they are described in WO-A 91/07874;

b) dichlorophenylpyrazolecarboxylic acid derivatives (i.e. of the formula (I) where W=(W2) and $(R^{17})_n=2,4-Cl_2$), preferably compounds such as ethyl 1-(2,4-dichlorophenyl)-5-methylpyrazole-3-carboxylate (I-2), ethyl 1-(2,4-dichlorophenyl)-5-isopropylpyrazole-3-carboxylate (I-3), ethyl 1-(2,4-dichlorophenyl)-5-(1,1-dimethylethyl)pyrazole-3-carboxylate (I-4), ethyl 1-(2,4-dichlorophenyl)-5-phenylpyrazole-3-carboxylate (I-5) and related compounds as they are described in EP-A-0 333 131 and EP-A-0 269 806;

c) compounds of the triazolecarboxylic acid type (i.e. of the formula (I) where W=(W3) and $(R^{17})_n=2,4-Cl_2$), preferably compounds such as fenchlorazole-ethyl, i.e. ethyl 1-(2,4-dichlorophenyl)-5-trichloromethyl-(1H)-1,2,4-triazole-3-carboxylate (I-6), and related compounds (see EP-A-0 174 562 and EP-A-0 346 620);

d) compounds of the 5-benzyl- or 5-phenyl-2-isoxazoline-3-carboxylic acid type or of the 5,5-diphenyl-2-isoxazoline-3-carboxylic acid type, such as isoxadifen (I-12), (where W=(W4)), preferably compounds such as ethyl 5-(2,4-dichlorobenzyl)-2-isoxazoline-3-carboxylate (I-7) or ethyl 5-phenyl-2-isoxazoline-3-carboxylate (I-8), and related compounds as they are described in WO-A-91/08202, or of the 5,5-diphenyl-2-isoxazolinecarboxylate type (I-9, isoxadifen-ethyl) or of the n-propyl 5,5-diphenyl-2-isoxazolinecarboxylate type (I-10) or of the ethyl 5-(4-fluorophenyl)-5-phenyl-2-isoxazoline-3-carboxylate type (I-11), as they are described in WO-A-95/07897.

e) Compounds of the 8-quinolinoxyacetic acid type, for example those of the formula (II), where $(R^{19})_n=5-Cl$, $R^{20}=OR^{24}$ and $T=CH_2$, preferably the compounds
1-methylhexyl (5-chloro-8-quinolinoxy)acetate (II-1, cloquintocet-mexyl),
1,3-dimethylbut-1-yl (5-chloro-8-quinolinoxy)acetate (II-2),
4-allyloxybutyl (5-chloro-8-quinolinoxy)acetate (II-3),
1-allyloxyprop-2-yl(5-chloro-8-quinolinoxy)acetate (II-4),
ethyl (5-chloro-8-quinolinoxy)acetate (II-5),
methyl (5-chloro-8-quinolinoxy)acetate (II-6),
allyl (5-chloro-8-quinolinoxy)acetate (II-7),
2-(2-propylideneiminooxy)-1-ethyl (5-chloro-8-quinolinoxy)acetate (II-8),
2-oxoprop-1-yl(5-chloro-8-quinolinoxy)acetate (II-9),
(5-chloro-8-quinolinoxy)acetic acid (II-10) and its salts as they are described for example in WO-A-2002/34048,
and related compounds as they are described in EP-A-0 860 750, EP-A-0 094 349 and EP-A-0 191 736 or EP-A-0 492 366.

f) Compounds of the (5-chloro-8-quinolinoxy)malonic acid type, i.e. of the formula (II) where $(R^{19})_n=5-Cl$, $R^{20}=OR^{24}$, $T=$—CH(COO-alkyl)-, preferably the compounds diethyl (5-chloro-8-quinolinoxy)malonate (II-11), diallyl (5-chloro-8-quinolinoxy)malonate, methyl ethyl (5-chloro-8-quinolinoxy)malonate and related compounds as they are described in EP-A-0 582 198.

g) Compounds of the dichloroacetamide type, i.e. of the formula (III), preferably:
N,N-diallyl-2,2-dichloroacetamide (dichlormid (III-1), from U.S. Pat. No. 4,137,070).
4-dichloroacetyl-3,4-dihydro-3-methyl-2H-1,4-benzoxazine (IV-2. Benoxacor, from EP 0 149 974),
N1,N2-diallyl-N2-dichloroacetylglycinamide (DKA-24 (III-3), from HU 2143821),
4-dichloroacetyl-1-oxa-4-aza-spiro[4,5]decane (AD-67).
2,2-dichloro-N-(1,3-dioxolan-2-ylmethyl)-N-(2-propenyl)acetamide (PPG-1292),
3-dichloroacetyl-2,2,5-trimethyloxazolidine (R-29148, III-4),
3-dichloroacetyl-2,2-dimethyl-5-phenyloxazolidine,
3-dichloroacetyl-2,2-dimethyl-5-(2-thienyl)oxazolidine,
3-dichloroacetyl-5-(2-furanyl)-2,2-dimethyloxazolidine (furilazole (III-5), MON 13900),
1-dichloroacetylhexahydro-3,3,8a-trimethylpyrrolo[1,2-a]pyrimidin-6(2H)-one (dicyclonon, BAS 145138), h) compounds from group (b), preferably
1,8-naphthalic anhydride (b-1),
methyldiphenyl methoxyacetate (b-2),
cyanomethoxyimino(phenyl)acetonitrile (cyometrinil) (b-3),
1-(2-chlorobenzyl)-3-(1-methyl-1-phenylethyl)urea (cumyluron) (b-4),
O,O-diethyl S-2-ethylthioethyl phosphorodithioate (disulfoton) (b-5),
4-chlorophenyl methylcarbamate (mephenate) (b-6),
O,O-diethyl O-phenyl phosphorothioate (dietholate) (b-7),
4-carboxy-3,4-dihydro-2H-1-benzopyran-4-acetic acid (CL-304415, CASReg. No: 31541-57-8) (b-8),
1,3-dioxolan-2-ylmethoxylmino(phenyl)acetonitrile (oxabetrinil) (b-9),
4'-chloro-2,2,2-trifluoroacetophenone O-1,3-dioxolan-2-ylmethyloxime (fluxofenim) (b-10),
4,6-dichloro-2-phenylpyrimidine (fenclorim) (b-11),
benzyl 2-chloro-4-trifluoromethyl-1,3-thiazole-5-carboxylate (flurazole) (b-12),
2-dichloromethyl-2-methyl-1,3-dioxolane (MG-191) (b-13), N-(4-methylphenyl)-N'-(1-methyl-1-phenylethyl)urea (dymron) (b-14),
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor) and their salts and esters, preferably ($C_1$-$C_8$).

Furthermore preferred compounds of the formula (IV) or their salts which are known as safeners are those in which $R^{30}$ is hydrogen, ($C_1$-$C_6$)alkyl, ($C_3$-$C_6$)cycloalkyl, furanyl or thienyl, where each of the 4 last-mentioned radicals is unsubstituted or substituted by one or more substituents selected from the group consisting of halogen, ($C_1$-$C_4$)alkoxy, halo($C_1$-$C_6$)alkoxy and ($C_1$-$C_4$)alkylthio and in the case of cyclic radicals also by ($C_1$-$C_4$)alkyl and ($C_1$-$C_4$)haloalkyl, $R^{31}$ is hydrogen, $R^{32}$ is halogen, halo($C_1$-$C_4$)alkyl, halo($C_1$-$C_4$)alkoxy, ($C_1$-$C_4$)alkyl, ($C_1$-$C_4$)alkoxy, ($C_1$-$C_4$)alkylsulfonyl, ($C_1$-$C_4$)alkoxycarbonyl or ($C_1$-$C_4$)alkylcarbonyl, preferably halogen, ($C_1$-$C_4$)haloalkyl, such as trifluoromethyl, ($C_1$-$C_4$)alkoxy, halo($C_1$-$C_4$)alkoxy, ($C_1$-$C_4$)alkoxycarbonyl or ($C_1$-$C_4$)alkylsulfonyl, $R^{33}$ is hydrogen, $R^{34}$ is halogen, ($C_1$-$C_4$)alkyl, halo($C_1$-$C_4$)alkyl, halo($C_1$-$C_4$)alkoxy, ($C_3$-$C_6$)cycloalkyl, phenyl, ($C_1$-$C_4$)alkoxy, cyano, ($C_1$-$C_4$)alkylthio, ($C_1$-$C_4$)alkylsulfinyl, ($C_1$-$C_4$)alkylsulfonyl, ($C_1$-$C_4$)alkoxycarbonyl or ($C_1$-$C_4$)alkylcarbonyl, preferably halogen, ($C_1$-$C_4$)alkyl, ($C_1$-$C_4$)haloalkyl such as trifluoromethyl, halo($C_1$-$C_4$)alkoxy, ($C_1$-$C_4$)alkoxy or ($C_1$-$C_4$)alkylthio, n is 0, 1 or 2 and
m is 1 or 2.

Especially preferred compounds of the formula (IV) which are known as safeners are those in which
$R^{30}$=$H_3C$—O—$CH_2$—, $R^{31}$=$R^{33}$=H, $R^{34}$=2-OMe (IV-1),
$R^{30}$=$H_3C$—O—$CH_2$—, $R^{31}$=$R^{33}$=H, $R^{34}$=2-OMe-5-Cl (IV-2),
$R^{30}$=cyclopropyl, $R^{31}$=$R^{33}$=H, $R^{34}$=2-OMe (IV-3),
$R^{30}$=cyclopropyl, $R^{31}$=$R^{33}$=H, $R^{34}$=2-OMe-5-Cl (IV-4),
$R^{30}$=cyclopropyl, $R^{31}$=$R^{33}$=H, $R^{34}$=2-Me (IV-5),
$R^{30}$=tert-butyl, $R^{31}$=$R^{33}$=H, $R^{34}$=2-OMe (IV-6).

Furthermore preferred compounds of the formula (V) which are known as safeners are those in which $X^3$ is CH;

$R^{35}$ is hydrogen, ($C_1$-$C_6$)alkyl, ($C_3$-$C_6$)cycloalkyl, ($C_2$-$C_6$)alkenyl, ($C_5$-$C_6$)cycloalkenyl, phenyl or 3- to 6-membered heterocyclyl having up to three heteroatoms selected from the group consisting of nitrogen, oxygen and sulfur, where the six last-mentioned radicals are optionally substituted by one or more identical or different substituents selected from the group consisting of halogen, ($C_1$-$C_6$)alkoxy, ($C_1$-$C_6$)haloalkoxy, ($C_1$-$C_2$)alkylsulfinyl, ($C_1$-$C_2$)alkylsulfonyl, ($C_3$-$C_6$)cycloalkyl, ($C_1$-$C_4$)alkoxycarbonyl, ($C_1$-$C_4$)alkylcarbonyl and phenyl and in the case of cyclic radicals also by ($C_1$-$C_4$)alkyl and ($C_1$-$C_4$)haloalkyl;

$R^{36}$ is hydrogen, ($C_1$-$C_6$)alkyl, ($C_2$-$C_6$)alkenyl, ($C_2$-$C_6$)alkynyl, where the three last-mentioned radicals are optionally substituted by one or more identical or different substituents selected from the group consisting of halogen, hydroxyl, ($C_1$-$C_4$)alkyl, ($C_1$-$C_4$)alkoxy and ($C_1$-$C_4$)alkylthio;

$R^{37}$ is halogen, ($C_1$-$C_4$)haloalkyl, ($C_1$-$C_4$)haloalkoxy, nitro, ($C_1$-$C_4$)alkyl, ($C_1$-$C_4$)alkoxy, ($C_1$-$C_4$)alkylsulfonyl, ($C_1$-$C_4$)alkoxycarbonyl or ($C_1$-$C_4$)alkylcarbonyl;

$R^{38}$ is hydrogen;

$R^{39}$ is halogen, nitro, ($C_1$-$C_4$)alkyl, ($C_1$-$C_4$)haloalkyl, ($C_1$-$C_4$)haloalkoxy, ($C_3$-$C_6$)cycloalkyl, phenyl, ($C_1$-$C_4$)alkoxy, cyano, ($C_1$-$C_4$)alkylthio, ($C_1$-$C_4$)alkylsulfinyl, ($C_1$-$C_4$)alkylsulfonyl, ($C_1$-$C_4$)alkoxycarbonyl or ($C_1$-$C_4$)alkylcarbonyl;

n is 0, 1 or 2 and
m is 1 or 2.

Preferred compounds of the formula (VI) which are known as safeners are (S3-1), (S3-2), (S3-3), (S3-4) and (S3-5).

Other preferred compounds of the formula (VII) are
1-[4-(N-2-methoxybenzoylsulfamoyl)phenyl]-3-methylurea (VII-1),
1-[4-(N-2-methoxybenzoylsulfamoyl)phenyl]-3,3-dimethylurea (VII-2),
1-[4-(N-4,5-dimethylbenzoylsulfamoyl)phenyl]-3-methylurea (VII-3) and
1-[4-(N-naphthoylsulfamoyl)phenyl]-3,3-dimethylurea (VII-4).

Likewise preferred compounds are those of the formulae VIII-1 to VIII-4

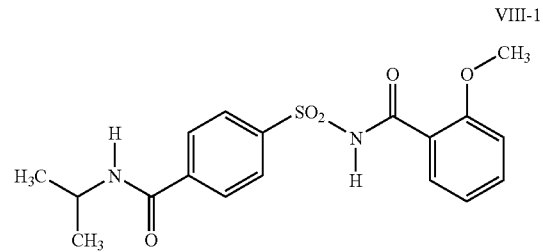

VIII-1

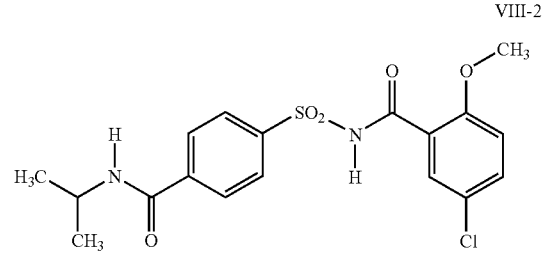

VIII-2

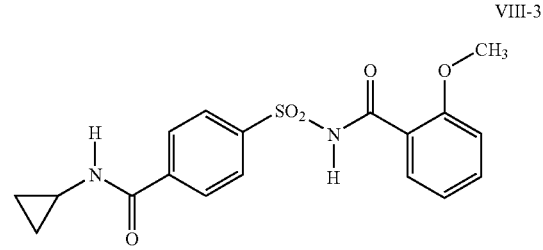

VIII-3

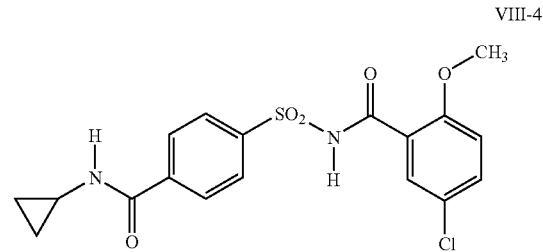

VIII-4 of which, in turn, the compound VIII-3 (4-cyclopropylaminocarbonyl-N-(2-methoxybenzoyl)benzenesulfonamide) is very especially preferred for use as agent for increasing the tolerance in plants to abiotic stress factors.

Especially preferred compounds for use as agents for increasing the tolerance in plants to abiotic stress factors are those which are selected from the group of compounds known as safeners which consists of the compounds of the formulae I-1 (mefenpyr-diethyl), I-9 (isoxadifen-ethyl), II-1 (chloquintocet-mexyl), b-11 (fenclorim), b-14 (dymron), and VIII-3 (4-cyclopropylaminocarbonyl-N-(2-methoxybenzoyl)benzenesulfonamide, with the compounds I-1 and VIII-3 being very especially preferred).

The compounds identified/mentioned above, which, under certain circumstances, may already be known as safeners, can already be employed in genetically modified plants.

The genetically modified plants (also referred to as transgenic plants) are, as a rule, distinguished by particular advantageous properties, for example by resistances to certain pesticides, especially certain herbicides, resistances to plant diseases or pathogen agents of plant diseases, such as certain insects or microorganisms such as fungi, bacteria or viruses. Other particular properties concern for example the harvested material with regard to quantity, quality, storage ability, composition and specific constituents. Thus, there are known transgenic plants with an increased starch content or a modified starch quality, or those where the harvested material has a different fatty acid composition.

Preferred is the use of the identified/mentioned compounds, which are known as safeners, or the salts of these compounds in economically important transgenic crops of useful plants and ornamentals, for example cereals such as wheat, barley, rye, oats, sorghum and millet, rice and maize or else crops of sugar beet, cotton, soya, oilseed rape, potato, tomato, pea and other vegetables, especially preferably in crops of maize, wheat, barley, rye, oats, rice, oilseed rape, sugar beet and soya, very especially preferably in crops of maize, wheat, rice, oilseed rape, sugar beet and soya.

In addition, transgenic plants can also be treated with substances identified with the aid of DNA microarrays, such as the molecules which are already known as safeners, whose tolerance to abiotic stress factors has already been increased as the result of recombinant methods, so that a synergistic effect of the endogenously encoded tolerance and the extraneously applied tolerance-increasing effect is observed.

Conventional ways of generating novel plants which have modified properties in comparison with existing plants are, for example, traditional breeding methods and the generation of mutants. As an alternative, novel plants with modified properties can be generated with the aid of recombinant methods (see, for example, EP-A-0221044, EP-A-0131624). The following have been described in a plurality of cases:
for example
recombinant modifications of crop plants in order to modify the starch synthesized in the plants (for example WO 92/11376, WO 92/14827, WO 91/19806),
transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659),
transgenic crop plants, for example cotton, with the ability to produce *Bacillus thuringiensis* toxins (Bt toxins), which make the plants resistant to certain pests (EP-A-0142924, EP-A-0193259),
transgenic crop plants with a modified fatty acid composition (WO 91/13972).
A large number of molecular-biological techniques with the aid of which novel transgenic plants with modified properties can be generated are known in principle; see, for example, Sambrook et al., 1989, Molecular Cloning, A Laboratory Manual, 2nd Edition, Cold Spring Harbor Laboratory Press, Cold Spring Harbor, N.Y.; or Winnacker "Gene und Klone", VCH Weinheim 2nd Edition, 1996 or Christou, "Trends in Plant Science" 1 (1996) 423-431).

To carry out such recombinant manipulations, nucleic acid molecules can be introduced into plasmids which permit a mutagenesis or a sequence modification by means of the recombination of DNA sequences. With the aid of the abovementioned standard methods, it is possible for example to carry out base substitutions, to remove part-sequences or to add natural or synthetic sequences. To link the DNA fragments with one another, adapters or linkers can be added to the fragments.

The generation of plant cells with a reduced activity of a gene product can be accomplished for example by expressing at least one suitable antisense RNA, a sense RNA for achieving a cosuppression effect or the expression of at least one suitably constructed ribosyme which specifically cleaves transcripts of the abovementioned gene product.

For this purpose, it is possible to use firstly DNA molecules which comprise all of the coding sequence of a gene product including any flanking sequences which are present, or else DNA molecules which only comprise parts of the coding sequence, it being necessary for these parts to be long enough in order to bring about an antisense effect in the cells. Also possible is the use of DNA sequences which have a high degree of homology with the coding sequences of a gene product, but which are not completely identical.

When expressing nucleic acid molecules in plants, the protein synthetized can be located in any compartment of the plant cell. In order to achieve the localization in a particular, compartment, however, it is possible for example to link the coding region with DNA sequences which ensure the localization in a particular compartment. Such sequences are known to a person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to give intact plants, using known techniques. The transgenic plants can, in principle, take the form of plants of any plant species, i.e. both monocots and dicots.

Thus, transgenic plants are obtainable which have modified properties as the result of the overexpression, suppression or inhibition of homologous (=natural) genes or gene sequences or the expression of heterologous (=foreign) genes or gene sequences.

Preferably, the molecules which have been identified with the aid of the DNA microarrays or which are known as safeners can be employed in transgenic crops which are resistant to herbicides from the group of the sulfonylureas, glufosinate-ammonium or glyphosate-isopropylammonium and analogous active substances and/or which have, as the result of recombinant modification, an endogenous tolerance to abiotic stress factors.

When applying the active substances according to the invention in transgenic crops, effects which are specific for the application in the transgenic crop in question are frequently observed in addition to the effects against harmful plants which can be observed in other crops; for example a modified or specifically widened weed spectrum which can be controlled, modification application rates which can be used for the application, preferably good combining ability with the herbicides to which the transgenic crop is resistant, and influencing the growth and yield of the transgenic crop plants.

The invention therefore also relates to the use of the compounds identified with DNA microarrays, or of compounds which are already known as safeners, for increasing the tolerance to abiotic stress factors in transgenic crop plants, preferably with the purpose of increasing the yield.

The present invention relates to a method of finding a compound which increases the tolerance to abiotic stress factors in plants, the increase in the transcription or expression of individual or more plant-endogenous genes, such as, for example, genes coding for proteins from the group of the cytochrome oxidases, such as cytochrome oxidase P450, glycosyltransferases, uricases, such as uricase II (E.C.17.3.3), peptidases, different membrane proteins, amidohydrolases and various general stress proteins, being regarded as proof for the induction.

The present invention particularly relates to a method of finding compounds which induce the transcription of the genes which code for plant-endogenous stress tolerance enzymes, which comprises:
a) exposing test plants to one or more abiotic stress factors,
b) bringing control plants, under otherwise identical conditions like the test plants of a), additionally into contact with a test compound, be it in the form of dressed seed material or be it by spraying with a particular development stage or else by uptake via the roots,
c) extracting RNA from the test plants and the control plants,
d) either labeling the RNA directly with a radiolabel or with a cold label, or else labeling the RNA with a radiolabel or a cold label while simultaneously transcribing it enzymatically into the corresponding cDNA, or else transcribing the resulting, unlabeled cDNA enzymatically into a corresponding radiolabeled or cold-labeled cRNA,
e) hybridizing a DNA microarray which comprises plant DNA sequences with the substances obtained in step d),
f) generating expression profiles of the genes for the expression of different stress proteins by comparing the plants tested in a) and b),
g) quantitatively determining the expression differentials measured in f), and
h) carrying out the cluster analysis of the expression profiles assigned in g) for a final classification.

In the case of the abovementioned step d), the enzymatic transcription of the resulting cDNA into a cRNA must be considered as the preferred process step since a further amplification of the hybridization sample can thereby be achieved. Likewise preferred is labeling by means of cold nucleotides, especially preferably labeling by means of biotinylated UTP and/or CTP, where the detection is carried out after the hybridization reaction by binding streptavidin-phycoerythrin as fluorophore to the biotinylated cRNA. A detection of the specific phycoerythrin fluorescence, which serves as the base for the quantitative determination of the expression differentials measured, is carried out after the hybridization step, with the aid of a laser scanner.

The present invention preferably relates to a process in which the abovementioned procedures a)-h) are maintained, where, in the case of the intended increase in the case of heat stress, the genes for the expression of the cytochrome oxidases, such as cytochrome oxidase P450, glycosyltransferases, uricases, such as uricase (E.C.17.3.3), peptidases, different membrane proteins, amidohydrolases in the case of heat-stressed and non-heat-stressed plants is compared, preferably of the genes for the expression of "N-carbamyl-L-amino acid amidohydrolase" (Zm.11840.1.A1_at), of "serine carboxypeptidase (Zm.18994.2.A1_a_at), of uricase II (E.C.1.7.3.3) and of glycosyltransferase (Zm.12587.1.S1_s_at), very especially preferably of the genes for the expression of "N-carbamyl-L-amino acid amidohydrolase" (Zm.11840.1.A1_at) and of "serine carboxypeptidase" (Zm.18994.2.A1_a_at) (signature as per maize genome array from Affymetrix (Affymetrix Inc., 3380 Central Expressway, Santa Clara, Calif., USA)), and where the gene expression in comparison with the heat-stressed control plant upon treatment with, is, for example, increased by a factor of 1.5 or more, preferably by a factor of 1.5 to 30, preferably 1.5 to 20, especially preferably 1.5 to 10, very especially preferably 1.5 to 5, where the increase in the modified expression profiles of individual genes independently of one another can be in the various ranges which have been mentioned above.

The present invention also preferably relates to a process in which the abovementioned process steps a)-h) are maintained, where, in the case of the intended increase in the case of drought stress for example the genes for the expression of the late embryogenesis abundant proteins such as the dehydrins, of the universal stress protein (Zm.818.1.A1_at), non-symbiotic hemoglobin (Zm.485.1.A1_at), the protein which is addressed as "Zm.818.2.A1_a_at" (maize genome array from Affymetrix (Affymetrix Inc., 3380 Central Expressway, Santa Clara, Calif., USA)) and of the protein addressed as "Zm.18682.1.A1_s_at" (maize genome array from Affymetrix (Affymetrix Inc., 3380 Central Expressway, Santa Clara, Calif., USA)) of drought-stressed and non-drought-stressed plants is compared, preferably the genes for the expression of the universal stress protein (Zm.818.1.A1_at), non-symbiotic hemoglobin (Zm.485.1.A1_at), of the protein addressed as "Zm.818.2.A1_a_at" (signature as per maize genome array from Affymetrix (Affymetrix Inc., 3380 Central Expressway, Santa Clara, Calif., USA)) and of the protein addressed as "Zm.18682.1.A1_s_at" (maize genome array from Affymetrix (Affymetrix Inc., 3380 Central Expressway, Santa Clara, Calif., USA)) where the gene expression in comparison with the drought-stressed control plant upon treatment with, is, for example, increased by a factor of 1.5 or more, preferably by a factor of 1.5 to 30, preferably 1.5 to 20, especially preferably 1.5 to 10, very especially preferably 1.5 to 8, where the increase in the modified expression profiles of individual genes independently of one another can be in the various ranges which have been mentioned above.

The present invention furthermore relates to the use of certain DNA microarrays which are used on the basis of genetic information from plants, preferably genetic information from useful plants, especially preferably from useful plants such as, for example, from maize, cereals such as wheat, barley, rye, oats, rice and soya, preferably from maize, wheat, barley, rye, rice and soya, especially preferably from barley, maize, wheat, rice and soya, very especially preferably from maize, wheat and soya, for finding modified gene expression patterns. Here, the relative changes of the gene patterns for genes of different stress proteins in plants treated with test compounds are compared with untreated control plants under otherwise identical stress conditions.

The invention furthermore relates to the use of the promoters of the indicator genes described in conjunction with specific reporter genes (for example GUS, GFP, luciferase and the like) for finding substances which have a positive effect on the abiotic stress tolerance in crop plants. Here, transgenic test plants are generated which comprise the abovementioned promoter/reporter gene constructs. Active substances which increase the abiotic stress tolerance of plants by the above-described mechanism induce the expression of the reporter gene and can be identified with the aid of a colorimetric, fluorimetric or other suitable assay.

The invention furthermore relates to the use of the described indicator genes for increasing the abiotic stress tolerance in transgenic crop plants. Here, the genes are fused with a suitable promoter which has the desired strength and specificity, and the constructs are transformed into monocotyledonous or dicotyledonous crop plants. The resulting transgenic plants are distinguished by an increased tolerance to abiotic stress, for example chill, heat, drought and the like.

The present invention furthermore also relates to the use of the compounds which have been identified with the aid of the DNA microarray taking into consideration the expression profiles of the genes and/or of compounds which are already known as safeners and which, in the case of abiotic stress conditions such as, for example, abiotic stress factors which act on this plant, such as temperature (chill, frost or heat), water (dryness or drought) or the chemical load (lack or excess of mineral salts, heavy metals, gaseous noxious substances), have a positive effect, i.e. an expression-enhancing effect, with regard to their inductive effect on single genes or a plurality of genes of the plant-endogenous defense mechanisms, such as, for example, in the case of heat stress on cytochrome oxidases such as cytochrome oxidase P450, on glycosyltransferases, on uricases such as uricase II (E.C.17.3.3), on peptidases, on different membrane proteins, on amidohydrolases and/or various stress proteins, and/or for example in the case of drought stress have a positive effect, i.e. an expression-enhancing effect, with regard to their inductive effect on single genes or a plurality of genes of the universal stress proteins, non-symbiotic hemoglobin (Zm.485.1.A1_at), of the protein addressed as "Zm.818.2.A1_a_at" (maize genome array from Affymetrix (Affymetrix Inc., 3380 Central Expressway, Santa Clara, Calif., USA)) and of the protein addressed as "Zm.18682.1.A1_s_at" (signature according to maize genome array from Affymetrix (Affymetrix Inc., 3380 Central Expressway, Santa Clara, Calif., USA)), as active substances for increasing the stress tolerance in useful plants.

The invention also relates to the use of substances identified with the aid of the DNA microarray and/or the molecules which are already known as safeners for increasing the tolerance to abiotic stress factors in various crop plants such as maize, cereals such as wheat, barley, rye, oats, rice and soya, preferably maize, wheat, barley, rye, rice and soya, especially preferably maize, wheat, rice and soya, very especially preferably maize, wheat and soya.

The present invention therefore also relates to the use of the compounds which have been identified with the aid of the DNA microarray taking into consideration the expression profiles of the genes and/or of compounds which are already known as safeners which, in plants, directly or indirectly, for example via a signal transduction chain, contribute to increasing the tolerance to abiotic stress factors, such as, for example, temperature (such as chill, frost or heat), water (such as dryness, drought or anoxia), or the chemical load (such as lack or excess of mineral salts, heavy metals, gaseous noxious substances), for increasing the yield, for extending the vegetation period, for making possible an earlier sowing date, for increasing the quality, or for use in plant breeding using otherwise less vital inbred lines.

The present invention therefore also relates to a method of increasing the yield in crops of useful plants, for extending the vegetation period, for making possible an earlier sowing date, for increasing the quality, or for use in plant breeding using otherwise less vital inbred lines which comprises treating the useful plants by seed dressing, by foliar sprays or by cell application with one or more compounds which have been identified with the aid of the DNA microarray and/or compounds which are already known as safeners.

Preferred in this context are those compounds whose use as what are known as safeners is already known in crop protection, such as, for example, from the group of the compounds known as safeners consisting of the compounds of the formulae I-1 (mefenpyr-diethyl), I-9 (isoxadifen-ethyl), II-1 (chloquintocet-mexyl), b-11 (fenclorim), b-14 (dymron), VIII-3 (4-cyclopropylaminocarbonyl-N-(2-methoxybenzoyl)benzenesulfonamide), very especially preferably the compounds I-1 and VIII-3 (4-cyclopropylaminocarbonyl-N-(2-methoxybenzoyl)benzenesulfonamide)).

By applying the abovementioned compounds individually or in combination, useful plants can be protected efficiently against the effects of abiotic stress factors, which manifests itself for example in higher yields.

The present invention therefore also relates to a method of increasing the tolerance of useful plants in crops of useful plants to abiotic stress factors by the individual or combined application of the compounds identified with the aid of the DNA microarray taking into consideration the expression profiles of the genes and/or of compounds which are already known as safeners.

The examples which follow describe the invention in detail.

EXAMPLE 1

Proof of the activity of safeners on plants which had been exposed to specific drought-stress conditions, by means of gene expression profiling (GFP):
Abiotic wtress factor=drought stress Maize seeds cv. Lorenzo were dressed with the compound 4-cyclopropylamino-carbonyl-N-(2-methoxybenzoyl)benzenesulfonamide (=VIII-3). To this end, 10 g of seeds were incubated with 20 mg of active substance dissolved in 2 ml of methylene chloride, with gentle shaking, until the solvent had evaporated (approx. 30 minutes). The seeds of the control group were only dressed with solvent. Thereafter, the treated seeds were placed into pots with compost (diameter: 10 cm, in each case 10 seeds per pot), and the maize seedlings were raised for 10 days in a controlled-environment chamber under defined light, moisture and temperature conditions [white light, long day (16 hours light, 8 hours dark), 70% atmospheric humidity, 24° C.]. In each case 2×10 pots were used for the control groups and for the drought stress experiment. While the plants were raised, they were watered from below for 20 minutes every 2 days by raising the water level in a tray. 10 days after the seeds had germinated, the maize plants were exposed to the drought stress. To this end, the plants of control group 1 (without dressing with active substance) and of the test group (with dressing with active substance) were only irrigated every 7 days as described above. In the case of the plants of control group 2 (without dressing with active substance) and of the test group 2 (with dressing with active substance), the normal irrigation regime was reclaimed. After 3 weeks of drought stress conditions, the experiment was evaluated as follows. The aerial plant parts were cut off and dried overnight at 50° C. On the next day, the foliar biomass was determined in [g] (dry matter) per pot.

The data were averaged over the in each case 10 pots of the plant group. The numerical values shown in table 1 are relative values in [%] relative to the data obtained with the control group 2 (without dressing with active substance, normal irrigation regime).

TABLE 1

Drought stress experiment with maize plants without and with dressing with active substance

| Plant group: | Treatment: | Relative dry matter [%]: |
|---|---|---|
| Control group 1 | −S/+D | 50 |
| Control group 2 | −S/−D | 100 |
| Test group 1 | +S/+D | 80 |
| Test group 2 | +S/−D | 100 |

S = compound VIII-3 (=4-cyclopropylaminocarbonyl-N-(2-methoxybenzoyl)benzenesulfonamide),
D = drought stress Without stress conditions, the average dry matter is the same plants from undressed seeds and from dressed seeds (control group 2, test group 2).

On average, the plants from the group which had been dressed with the compound VIII-3 (=4-cyclopropylaminocarbonyl-N-(2-methoxybenzoyl)benzenesulfonamide) showed a more compact habit than the plants from the control group which, however, had no effect on the dry matter. Under drought stress, however, the average foliar biomass (dry matter) of the active-substance-dressed plants was significantly increased over the undressed control plant (control group 1, test group 1).

EXAMPLE 2

Abiotic Stress Factor=Heat Stress

Maize seeds cv. Lorenzo were dressed as in example 1 with the compound 4-cyclopropylaminocarbonyl-N-(2-methoxybenzoyl)benzenesulfonamide (=VIII-3) or treated only with solvent without active substance. The seedlings were raised for 10 days in the controlled-environment chamber under defined conditions, likewise as described in example 1. 2×10 pots with maize plants were used for the heat stress experiment. The control group consisted of undressed plants (solvent), the test group of plants which had been dressed with active substance. To apply the heat stress conditions, both plant groups were placed for 2 days into a controlled-environment cabinet at 45° C., white light, long day (16 hours light, 8 hours dark) and 70% atmospheric humidity. To avoid desiccation as the result of the high temperature, the plants were irrigated once per day from below by raising the water level in a tray. After the heat stress, it was observed that— especially in the control group—the shoots of many plants had collapsed and that the leaves were lying flat on the ground.

The experiment was valued quantitatively, taking into consideration the following criteria.

After the heat treatment, the plants which had collapsed were counted and the result per pot was assessed:

| <20% of the emerged plants collapsed: some damage | ○ |
| 20-50% of the emerged plants collapsed: medium damage | ◉ |
| >50% of the emerged plants collapsed: severe damage | ● |

Thereafter, all plants were grown on for 2 weeks under standard conditions. Then, the length increment of the individual plants was measured, and the survival rate of the plants per pot was determined:

| >50% survival rate: some damage | ○ |
| 20-50% survival rate: medium damage | ◉ |
| <20% survival rate: severe damage | ● |

The results of the evaluation of the experiment are compiled in table 2.

The undressed control plants were severely damaged by the heat stress. What was noticeable was in particular the collapse of the shoots in the case of most plants and the poor survival rate. The test plants which had been dressed with active substance were distinguished in particular by considerably better "standing". While the final score highlights the damage caused by the severe heat stress even in those plants, their survival rate was significantly higher than in the control group.

TABLE 2

Dried-stress experiments with maize plants with or without dressing with active substance

| Plant group: | Treaetment: | |
|---|---|---|
| Control group | −S/+H | Interim score (collapsed plants):<br>● ● ● ● ● ● ○ ○ ○<br>Final score (survival rate):<br>● ● ● ● ● ● ● ● ○ |
| Test group | +S/+H | Interim score (collapsed plants):<br>○ ○ ○ ○ ○ ○ ○ ○ ○<br>Final score (survival rate):<br>● ● ● ● ◉ ◉ ◉ ◉ ◉ |

S = compound VII-3 (=4-cyclopropylaminocarbonyl-N-(2-methoxybenzoyl)benzenesulfonamide),
H = heat stress

EXAMPLE 3

Abiotic Stress Factor=Chill Stress (Greenhouse)

Maize seeds cv. Lorenzo were sown into 10-cm-pots into compost at a rate of 10 seeds per pot. All experimental groups consisted of in each case 4 pots. The sown seeds of test groups 1 and 2 were sprayed pre-emergence with 50 and 100 [g a.i./ha], respectively, of the compound 4-cyclopropylaminocarbonyl-N-(2-methoxybenzoyl)benzenesulfonamide (=VIII-3). The seeds of the control group remained untreated. The plants were raised under controlled conditions in a controlled-environment chamber [white light (long day: 16 h light, 8 h dark), 22° C. day-time temperature, 14° C. night-time temperature, 60% atmospheric humidity]. After germination, when the plants had attained a length of approx. 1 cm, 2 pots from each group were incubated for 6 h in a different controlled-environment chamber under chill-stress conditions at −2° C. Thereafter, these plants were returned to the others in the first controlled-environment chamber.

After a further 24 hours under standard conditions, the experiment was evaluated. It was observed that the chill stress caused chloroses at the leaf tips of the seedlings of the untreated control group. These symptoms were either absent or only very weakly pronounced on the plants which had been treated with the active substance. None of the plants from the test groups of the control group which had been kept exclusively under standard conditions without chill stress showed any damage symptoms whatsoever.

To evaluate the experiment quantitatively, the plants with chloroses of the leaf tips were counted. The total number of the plants per test group and cold stress treatment was 20, provided over 2 pots in each case.

The results of the evaluation of the experiment are compiled in table 3.

TABLE 3

Chill-stress experiment (greenhouse) with maize plants without and with treatment with the active substance, compound VIII-3 (=4-cyclopropylaminocarbonyl-N-(2-methoxybenzoyl)benzenesulfonamide), pre-emergence. All plants were exposed to chill-stress treatment. The total number of plants per group was 20.

| Plant group: | Treatment with active substance (pre-emergence) [g a.i./ha]: | Number of damaged plants (chloroses): |
|---|---|---|
| Control group | 0 | 9 |
| Test group 1 | 50 | 1 |
| Test group 2 | 100 | 0 |

The results demonstrate that the treatment with the active substance VIII-3 (=4-cyclopropylaminocarbonyl-N-(2-methoxybenzoyl)benzenesulfonamide) can markedly reduce the damage symptoms which are the result of chill stress, or, at the higher dosage rate, completely prevents the occurrence of these symptoms.

EXAMPLE 4

Abiotic Stress Factor=Chill Stress (Field)

Maize seeds (dent corn) were dressed with 0.003 mg and 0.03 mg of the compound 4-cyclopropylaminocarbonyl-N-(2-methoxybenzoyl)benzenesulfonamide (=VIII-3) per g of seeds and sown into test plots, each of which measure 34 m$^2$ in size. One control plant contains untreated seed. Approximately 8 days after the seed emerged, the seedlings were in the one-leaf stage and were exposed for 5 days to the following temperature conditions:

| | Maximum: | Minimum: |
|---|---|---|
| Day 1: | 16.1° C. | 7.2° C. |
| Day 2: | 17.8° C. | 2.7° C. |
| Day 3: | 16.7° C. | 0.6° C. |
| Day 4: | 16.7° C. | 1.1° C. |
| Day 5: | 22.8° C. | 12.2° C. |

After this chill period, the test plots were scored. For this purpose, all plants were assessed individually, and plants with at least 20% chill symptoms based on the total leaf area (burns and/or chloroses) were considered to be damaged.

The results are compiled in table 4. In the control plot without dressing with active substance, all plants (100%) showed the above-described chill symptoms. In the test plots with dressing with active substance, the chill damage was significantly reduced. Here, only approximately 12% of the plants showed damage symptoms. The maximum frost-protection effect was attained in the range of the active substance quantities which had been used for the dressing, as shown in the table.

TABLE 4

Chill stress experiment (field) with maize plants without and with dressing with the active substance VIII-3 (=4-cyclopropylaminocarbonyl-N-(2-methoxybenzoyl)benzenesulfonamide)

| Plant group: | Chill damage [%]*: |
|---|---|
| Untreated | 100 |
| Dressed with 0.003 mg of (VIII-3 = 4-cyclopropylaminocarbonyl-N-(2-methoxybenzoyl)benzenesulfonamide) per seed | 12 |
| Dressed with 0.03 mg VIII-3 (=4-cyclopropylaminocarbonyl-N-(2-methoxybenzoyl)benzenesulfonamide) per seed | 12 |

*Number of plants with chill damage > 20% best of the total number of plants in the test plot

EXAMPLE 5

Characterization of Genes which are Induced by Test Substances Under Abiotic Stress Conditions, Measured by Gene Expression Profiling (GEP)

Maize seeds cv. Lorenzo were dressed as described in example 1 with the compound VIII-3 (=4-cyclopropylaminocarbonyl-N-(2-methoxybenzoyl)benzenesulfonamide) or with solvent. The plants were raised for 10 days in a controlled-environment chamber (conditions: see example 1). Thereafter, the plants were exposed to the following stress conditions:

(1) Heat stress: 6 h at 45° C.
(2) Drought stress: 7 days without irrigation, 24° C.

The control plants of the specific experimental group were kept under the standard conditions described in example 1 (temperature, irrigation).

After the stress treatment, the leaves of the stressed plants and of the unstressed control plants were harvested, shock-frozen in liquid nitrogen and stored at −80° C. until processed. All experiments were carried out in replications of in each case 2 pots.

The labeled RNA probes for the DNA chip hybridization were prepared as described in the protocols (Expression Analysis, Technical Manual) from Affymetrix (Affymetrix Inc., 3380 Central Expressway, Santa Clara, Calif., USA). First, total RNA was isolated from in each case 500 mg of the harvested leaves. In each case 10 μg of total RNA were used for the cDNA first- and second-strand synthesis. The cDNA was amplified with T7 polymerase and simultaneously labeled with biotin-UTP. In each case 20 μg of this biotinylated cDNA were employed for the hybridization of the maize genome array from Affymetrix. This DNA microarray contains DNA sequences whose totality represents 13339 genes. Thereafter, the DNA microarrays were washed in the Affymetrix Fluidics Station, stained with streptavidin/phycoerythrin (Molecular Probes, P/N S-866) and scanned with the appropriate Agilent Laser Scanner (Agilent Gene Array Scanner). The fluorescence data obtained were analyzed using Affymetrix's Microarray Suite 5 software. After the quality assurance had been performed, all DNA chip analyses were stored in a database. To determine relevant expression values (induction factors, repression factors), the absolute expression values of the genes from the respective stress experiments were compared with the values of the respective control experiments (i.e. without abiotic stress and solvent-dressing only), based on the scoring function predetermined by the Affymetrix software. The resulting 4 expression values per gene were averaged by calculating the median value. These median values are shown in the results tables as induction factors. Similarity comparisons of expression profiles of various experiments and cluster analyses were carried out using the "genedata expressionist" software from Genedata (Genedata, Maulbeerstr. 46, CH-4016 Basel, Switzerland).

The analysis of the expression profiles specifically searched for genes which are induced by the test substances only in conjunction with abiotic stress, but not by the substances or by stress alone. Such genes can be considered as indicators for additional anti-stress effects of the substances which exceed the known safener effect. The results from the analyses are shown in the tables which follow. The induction patterns of the indicator genes described permit the targeted finding of active substances for increasing the abiotic stress tolerance in crop plants.

a) Under heat stress conditions, i.e. the tested maize plants (dressed with 2 mg a.i. 4-cyclopropylaminocarbonyl-N-(2-methoxybenzoyl)benzenesulfonamide/g seeds) were exposed to a temperature of 45° C. for 6 hours 7 days after germination.

An overview over the induced gene groups revealed the following pattern, which is shown in table 5:

TABLE 5

| Sample Set No. | Condition A | Condition B | Condition C |
|---|---|---|---|
| Zm.11840.1.A1_at | 1.74 | 1.75 | 4.10 |
| Zm.4274.1.S1_at | 1.32 | 1.22 | 1.93 |
| Zm.3040.1.S1_at | 1.52 | 1.33 | 2.48 |
| Zm12587.1.S1.s_at | 1.30 | 1.45 | 2.33 |
| Zm18994.2.A1_a_at | 1.16 | 1.46 | 2.66 |
| Zm.13498.1.S1_at | 2.56 | 1.73 | 4.45 |

The respective sample set no. corresponds to:

| | |
|---|---|
| Zm.11840.1.A1_at: | putative N-carbamyl-L-amino acid amidohydrolase |
| Zm.4274.1.S1_at: | cytochrome P450 |
| Zm.3040.1.S1_at | uricase II (E.C.1.7.3.3); nodule specific uricase |
| Zm12587.1.S1.s_at: | glycosyltransferase |
| Zm18994.2.A1_a_at: | putative serine transferase |
| Zm.13498.1.S1_at: | membrane protein |

Condition A: heat stress (6 hours, 45° C.)
Condition B: Seeds dressed with 4-cyclopropylaminocarbonyl-N-(2-methoxybenzoyl)benzenesulfonamide (VII-3)/ NO heat stress
Condition C: Seeds dressed with 4-cyclopropylaminocarbonyl-N-(2-methoxybenzoyl)benzenesulfonamide (VIII-3)+ heat stress (6 hours, 45° C.).

Ignoring a slight basal induction of the analyzed gene activities, a pronounced increase in the gene expression was observed in all cases and is, in the case of the genes mentioned here, in the range of from 1.5 to 2.35 (expression under condition C/expression under condition A). If the test compound VIII-3 was tested on its own, i.e. without heat stress, the measured expression levels were in the range of the range induced by heat stress, or below or slightly above the range induced by heat stress.

The induction patterns derived from table 5 and which are shown directly by the resulting expression values show characteristic inductions by the action of the compound 4-cyclopropylaminocarbonyl-N-(2-methoxybenzoyl)benzenesulfonamide (=VIII-3), the effect on the putative N-carbamyl-L-amino acid amidohydrolase [Zm.11840.1.A1_at] and on the putative serine carboxypeptidase [Zm18994.2.A1-at] being most pronounced.

b) Under dried stress conditions, i.e. the tested maize plants (dressed with 2 mg a.i. 4-cyclopropylaminocarbonyl-N-(2-methoxybenzoyl)benzenesulfonamide/g seeds) were exposed to a temperature of 24° C. for 7 hours 7 days after germination.

An overview over the induced gene groups revealed the following pattern, which is shown in table 6:

TABLE 6

| Sample Set No. | Condition A | Condition B | Condition C |
|---|---|---|---|
| Zm.818.1.A1_at | 1.06 | 1.12 | 8.47 |
| Zm.3633.4.A1_at | 1.12 | 0.74 | 3.03 |
| Zm.18273.1.S1_at | 1.66 | 0.95 | 2.91 |
| Zm.13229.1.S1_at | 1.55 | 1.02 | 3.39 |
| Zm.12035.1.A1_at | 1.86 | 0.90 | 3.66 |
| Zm.485.1.A1_at | 0.89 | 1.00 | 5.49 |
| Zm.818.2.A1_at | 0.93 | 1.10 | 5.40 |
| Zm.10097.1.A1_at | 1.23 | 1.27 | 3.29 |
| Zm.18682.1.A1_at | 1.25 | 1.12 | 4.19 |

The respective sample set no. corresponds to:

| | |
|---|---|
| Zm.818.1.A1_at | universal stress protein |
| Zm.3633.4.A1_at | wound induced protein (fragment) |
| Zm.18273.1.S1_at | regulatory protein-like |
| Zm.13229.1.S1_at | NBS-LRR type disease resistance protein O2 (fragment) |
| Zm.12035.1.A1_at | similar to AT3G10120 |
| Zm.485.1.A1_at | non-symbiotic hemoglobin (HBT) (ZEAMP GLB1) |
| Zm.818.2.A1_at | expressed protein |
| Zm.10097.1.A1_at | expressed protein |
| Zm.18682.1.A1_at | unknown protein |

Condition A: drought stress (7 days, 24° C.)
Condition B: Seeds dressed with 4-cyclopropylaminocarbonyl-N-(2-methoxybenzoyl)benzenesulfonamide (VII-3)/ NO drought stress
Condition C: Seeds dressed with 4-cyclopropylaminocarbonyl-N-(2-methoxybenzoyl)benzenesulfonamide (VII-3)+ drought stress (7 days, 24° C.).

Ignoring a slight basal induction of the analyzed gene activities, a pronounced increase in the gene expression was observed in all cases and is, in the case of the genes mentioned here, in the range of from 1.75 to 8.0 (expression under condition C/expression under condition A). If the test compound VIII-3 was tested on its own, i.e. without heat stress, the measured expression levels were in the range of the range induced by dried stress, or in some cases even below the expression of unstressed plants (at values<1.0).

The induction patterns derived from table 6 and which are shown directly by the resulting expression values show characteristic inductions in the presence of the compound 4-cyclopropylaminocarbonyl-N-(2-methoxybenzoyl)benzenesulfonamide, the effect on the universal stress protein [Zm.818.1A1_at] and non-symbiotic hemoglobin (HBT) (ZEAMP GLB1) [Zm.485.1A1_at] being most pronounced.

We claim:

1. A method of increasing the yield of crop plants that are exposed to drought and/or heat stress, which comprises treating the seeds to be grown to said crop plants that will be exposed to drought and/or heat stress with mefenpyr-diethyl, thereby increasing the yield of said crop plants as compared to crop plants grown from the same seeds untreated with mefenpyr-diethyl and grown under the same environmental conditions.

2. A method of increasing the yield of crop plants that are exposed to drought and/or heat stress, which comprises treating the crop plants by foliar spray or by soil application with mefenpyr-diethyl, thereby increasing the yield of said crop plants.

\* \* \* \* \*